(12) United States Patent
Jung et al.

(10) Patent No.: US 9,345,244 B2
(45) Date of Patent: May 24, 2016

(54) PLANT GROWTH REGULATING COMPOUNDS

(75) Inventors: Pierre Joseph Marcel Jung, Stein (CH); Joerg Leipner, Stein (CH); Mathilde Denise Lachia, Stein (CH); Alain De Mesmaeker, Stein (CH); Matthew Murdoch Woodhead McLachlan, Bracknell Berkshire (GB)

(73) Assignees: Syngenta Participations AG, Basel (CH); Syngenta Limited, Guildford (GB)

( * ) Notice: Subject to any disclaimer, the term of this patent is extended or adjusted under 35 U.S.C. 154(b) by 0 days.

(21) Appl. No.: 14/344,765

(22) PCT Filed: Sep. 11, 2012

(86) PCT No.: PCT/EP2012/067706
§ 371 (c)(1),
(2), (4) Date: Apr. 2, 2014

(87) PCT Pub. No.: WO2013/037755
PCT Pub. Date: Mar. 21, 2013

(65) Prior Publication Data
US 2015/0005167 A1    Jan. 1, 2015

(30) Foreign Application Priority Data
Sep. 16, 2011 (EP) ................. 11181635

(51) Int. Cl.
*C07D 213/00* (2006.01)
*A01N 43/40* (2006.01)
*C07D 213/75* (2006.01)
*C07D 213/85* (2006.01)

(52) U.S. Cl.
CPC ............ *A01N 43/40* (2013.01); *C07D 213/75* (2013.01); *C07D 213/85* (2013.01)

(58) Field of Classification Search
CPC ........................................ C07D 213/75
USPC ............................................ 546/309
See application file for complete search history.

(56) References Cited

U.S. PATENT DOCUMENTS 7,799,812 B2 * 9/2010 Albert et al. ............... 514/364

FOREIGN PATENT DOCUMENTS

| WO | 2008049729 | 5/2008 | |
| WO | WO 2009109570 | * 9/2009 | C07D 213/75 |

OTHER PUBLICATIONS

Chemical Catalog, Sep. 2009 Supplier Otava.*
Database Registry [online], Chemical Abstrats Service, Columbus, OH, US; Sep. 9, 2011; Database Accession No. 1181390-80-6.
Database Registry [online], Chemical Abstracts Service, Columbus, Ohio, US, Sep. 8, 2009, Database Accession No. 1181342-17-5.

* cited by examiner

*Primary Examiner* — Nizal Chandrakumar
(74) *Attorney, Agent, or Firm* — R. Kody Jones

(57) ABSTRACT

The present invention relates to novel non-steroidal brassinosteroid mimetic derivatives, to processes and intermediates for preparing them, to plant growth regulator compositions comprising them and to methods of using them for controlling the growth of plants and/or promoting the germination of seeds.

5 Claims, No Drawings

PLANT GROWTH REGULATING COMPOUNDS

RELATED APPLICATION INFORMATION

This application is a 371 of International Application No. PCT/EP2012/067706, filed 11 Sep. 2012, which claims priority to EP Patent Application No. 11181635.1, filed 16 Sep. 2011, the contents of which are incorporated herein by reference herein.

The present invention relates to novel non-steroidal brassinosteroid mimetic derivatives, to processes and intermediates for preparing them, to plant growth regulator compositions comprising them and to methods of using them for controlling the growth of plants and/or promoting the germination of seeds.

Various chemical derivatives that act on the brassinosteroid signalling pathway have been described, for example, in Bioorg. Med. Chem. (1998), 6, p. 1975; Bioorg. Med. Chem. Let. (1999), 9, p. 425; J. Agric. Food Chem. (2002), 50, p. 3486; Planta (2001), 213, p. 716; WO2008/049729, WO2009/109570 and Chemistry & Biology (2009), 16, p. 594-604. Brassinosteroids and analogs thereof have been described to have useful plant growth regulating properties.

It has now surprisingly been found that certain new non-steroidal brassinosteroid mimetic derivatives have properties that are useful for controlling the growth of plants and/or promoting the germination of seeds. Preferably, the new compounds may result in improved plant growth properties, such as faster growth, faster germination, earlier germination and/or reduced toxicity. The compounds may offer other advantages such as enhances solubility, or be more advantageously formulated, provide more efficient delivery to the plant, provide improved uptake into the plant, or be more readily biodegradable.

According to the present invention, there is provided a compound of formula (I)

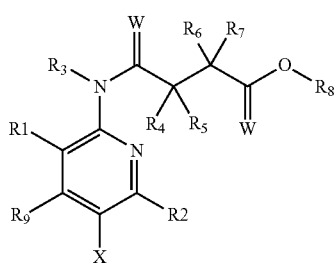

wherein
each W is independently O or S;
$R_1$, $R_2$ and $R_9$ are independently H, $C_1$-$C_6$haloalkyl, $C_1$-$C_6$alkoxy, cyano, halogen, $C_1$-$C_6$alkyl or $C_1$-$C_6$alkyl substituted by one or more hydroxyl, amine;
X is halogen, $C_1$-$C_6$haloalkyl, cyano, thiocyanate, nitro, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $C_2$-$C_6$alkenyl, $C_2$-$C_6$alkynyl, amine, N—$C_1$-$C_6$alkyl amine, N,N-di-$C_1$-$C_6$alkyl amine, $C_1$-$C_6$alkylcarbonyl, $C_1$-$C_6$alkoxycarbonyl, $C_1$-$C_6$haloalkoxycarbonyl, $C_1$-$C_6$haloalkylcarbonyl, $C_3$-$C_8$cycloalkyl, formyl, mercapto; or X is heteroaryl or heteroaryl substituted by one or more halogen, cyano, $C_1$-$C_3$alkyl, $C_1$-$C_3$haloalky;
and provided that when X is halogen, $R_2$, $R_3$, $R_4$, $R_5$, $R_6$, $R_7$, $R_9$ are hydrogen, both W are oxygen, and $R_8$ is hydrogen, methyl, ethyl, propyl or C2-C3alkyl substituted by one or two of hydroxyl, halogen or amine,
then $R_1$ is not hydrogen, $C_1$-$C_2$ alkyl or $C_2$ alkyl substituted by one or two of halogen, hydroxyl or amine;
$R_3$ is H, $C_1$-$C_6$alkyl, $C_1$-$C_6$haloalkyl, $C_1$-$C_6$alkylcarbonyl, $C_1$-$C_6$alkoxycarbonyl; or $R_3$ is $C_1$-$C_6$alkyl substituted by one or more cyano, amine, carbonylamine;
$R_4$, $R_5$, $R_6$ and $R_7$ are independently hydrogen, halogen, nitro, cyano, $C_1$-$C_6$alkyl, $C_1$-$C_6$haloalkyl, $C_1$-$C_6$alkoxy, hydroxyl, —OC(O)$R_{10}$, amine, N—$C_1$-$C_6$alkyl amine, or N,N-di-$C_1$-$C_6$ alkyl amine;
$R_8$ is hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_4$-$C_6$alkylcycloalkyl, benzyl or benzyl substituted by one to five substituents $R_{11}$, aryl or aryl substituted by one to five substituents $R_{11}$, heteroaryl or heteroaryl substituted by one to five substituents $R_{11}$, heterocyclyl or heterocyclyl substituted by one to five substituents $R_{11}$;
or $R_8$ is $C_1$-$C_6$ alkyl substituted by one or more cyano, nitro, amine, N—$C_1$-$C_6$alkyl amine, N,N-di-$C_1$-$C_6$alkyl amine, hydroxyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, benzyl or benzyl substituted by one to five substituents $R_{11}$, aryl or aryl substituted by one to five substituents $R_{11}$, heteroaryl or heteroaryl substituted by one to five substituents $R_{11}$, heterocyclyl or heterocyclyl substituted by one to five substituents $R_{11}$;
$R_{10}$ is hydrogen, $C_1$-$C_6$alkyl, $C_1$-$C_6$alkoxy, or $C_1$-$C_6$haloalkyl; and
each $R_{11}$ is independently cyano, nitro, amino, hydroxy, halogen, $C_1$-$C_6$alkyl, $C_1$-$C_6$haloalkyl, $C_1$-$C_4$alkoxy-$C_1$-$C_4$alkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_3$-$C_6$halocycloalkyl, $C_1$-$C_6$alkoxy, $C_1$-$C_6$haloalkoxy, $C_1$-$C_4$alkoxy-$C_1$-$C_4$-alkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, N—$C_1$-$C_6$alkylamino, N,N-di-($C_1$-$C_6$alkyl)amino, N,N-di-($C_1$-$C_6$alkyl)aminocarbonyl, N,N-di-($C_1$-$C_6$alkyl)aminosulfonyl, $C_1$-$C_6$alkylcarbonyl, $C_1$-$C_6$alkylcarbonyloxy, $C_1$-$C_6$alkoxycarbonyl, $C_1$-$C_6$alkylcarbonylamino;
or salts or N-oxides thereof;
and excluding the following compounds wherein
X is trifluoromethyl, $R_1$ is chlorine, $R_2$, $R_3$, $R_4$, $R_5$, $R_6$, $R_7$, $R_8$, $R_9$ are hydrogen, and both W are oxygen;
X is chlorine or bromine, $R_1$, $R_2$, $R_3$, $R_5$, $R_6$, $R_7$, $R_8$, $R_9$ are hydrogen, $R_4$ is amine, and both W are oxygen;
X is iodine or bromine, $R_1$, $R_3$, $R_4$, $R_5$, $R_6$, $R_7$, $R_9$ are hydrogen, $R_2$ and $R_8$ are methyl, and both W are oxygen;
X is bromine, $R_1$, $R_2$, $R_4$, $R_5$, $R_6$, $R_7$, $R_9$ are hydrogen, $R_3$ is ethyl, $R_8$ is methyl, and both W are oxygen;
And X is nitro, N—$C_1$-$C_6$alkyl amine or N,N-di-$C_1$-$C_6$alkyl amine, $R_1$, $R_2$, $R_3$, $R_4$, $R_5$, $R_6$, $R_7$, $R_8$, $R_9$ are hydrogen, and both W are oxygen.

Compounds according to formula (I') can be used in a plant growth regulator or seed germination promoting composition or as a plant growth regulator or a seed germination promoter, wherein formula (I') is the same as formula (I), but only with the following provisos:
that when X is halogen, $R_2$, $R_3$, $R_4$, $R_5$, $R_6$, $R_7$, $R_9$ are hydrogen, both W are oxygen, and $R_8$ is hydrogen, methyl, ethyl, propyl or $C_2$-$C_3$alkyl substituted by one or two of hydroxyl, halogen or amine, then $R_1$ is not hydrogen, $C_1$-$C_2$ alkyl or $C_2$ alkyl substituted by one or two of halogen, hydroxyl or amine;
and that the following compound is excluded wherein
X is nitro, $R_1$, $R_2$, $R_3$, $R_4$, $R_5$, $R_6$, $R_7$, $R_8$, $R_9$ are hydrogen, and both W are oxygen.

The following compounds are thus included in formula (I'):
X is trifluoromethyl, $R_1$ is chlorine, $R_2$, $R_3$, $R_4$, $R_5$, $R_6$, $R_7$, $R_8$, $R_9$ are hydrogen, and both W are oxygen;
X is chlorine or bromine, $R_1$, $R_2$, $R_3$, $R_5$, $R_6$, $R_7$, $R_8$, $R_9$ are hydrogen, $R_4$ is amine, and both W are oxygen;
X is iodine or bromine, $R_1$, $R_3$, $R_4$, $R_5$, $R_6$, $R_7$, $R_9$ are hydrogen, $R_2$ and $R_8$ are methyl, and both W are oxygen;
X is bromine, $R_1$, $R_2$, $R_4$, $R_5$, $R_6$, $R_7$, $R_9$ are hydrogen, $R_3$ is ethyl, $R_8$ is methyl, and both W are oxygen;
And X is N—$C_1$-$C_6$alkyl amine or N,N-di-$C_1$-$C_6$alkyl amine, $R_1$, $R_2$, $R_3$, $R_4$, $R_5$, $R_6$, $R_7$, $R_8$, $R_9$ are hydrogen, and both W are oxygen.

In other embodiments of formula (I) and formula (I'), when X is halogen, $R_1$ is not hydrogen, $C_1$-$C_2$ alkyl or $C_2$ alkyl substituted by one or more of halogen, hydroxyl or amine.

The compounds of formula (I) or (I') may exist in different geometric or optical isomers (diastereoisomers and enantiomers) or tautomeric forms. This invention covers all such isomers and tautomers and mixtures thereof in all proportions as well as isotopic forms such as deuterated compounds. The invention also covers all salts, N-oxides, and metalloidic complexes of the compounds of formula (I) or (I').

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are preferably $C_1$ to $C_6$ alkyl groups, more preferably $C_1$-$C_4$ and most preferably $C_1$-$C_3$ alkyl groups.

Each alkenyl moiety either alone or as part of a larger group (such as alkoxy, alkoxycarbonyl, alkylcarbonyl, alkylaminocarbonyl, dialkylaminocarbonyl) is having at least one carbon-carbon double bond and is, for example, vinyl, allyl. The Alkenyl groups are preferably $C_2$ to $C_6$alkenyl groups, more preferably $C_2$-$C_4$alkenyl groups.

Each alkynyl moiety either alone or as part of a larger group (such as alkoxy, alkoxycarbonyl, alkylcarbonyl, alkylaminocarbonyl, dialkylaminocarbonyl) is having at least one carbon-carbon triple bond and is, for example, ethynyl, propargyl. The Alkynyl groups are preferably $C_2$ to $C_6$alkynyl groups, more preferably $C_2$-$C_4$alkynyl groups. The term "alkynyl", as used herein, unless otherwise indicated, includes alkyl moieties having at least one carbon-carbon triple bond wherein alkyl is as defined above.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, —$CF_3$, —$CF_2Cl$, —$CH_2CF_3$ or —$CH_2CHF_2$.

Hydroxyalkyl groups are alkyl groups which are substituted with one or more hydroxyl group and are, for example, —$CH_2OH$, —$CH_2CH_2OH$ or —$CH(OH)CH_3$.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

Unless otherwise indicated, alkenyl and alkynyl, on their own or as part of another substituent, may be straight or branched chain and may preferably contain 2 to 6 carbon atoms, preferably 2 to 4, more preferably 2 to 3, and where appropriate, may be in either the (E)- or (Z)-configuration. Examples include vinyl, allyl and propargyl.

Unless otherwise indicated, cycloalkyl may be mono- or bi-cyclic, may be optionally substituted by one or more $C_1$-$C_6$alkyl groups, and preferably contain 3 to 7 carbon atoms, more preferably 3 to 6 carbon atoms. Examples of cycloalkyl include cyclopropyl, 1-methylcyclopropyl, 2-methylcyclopropyl, cyclobutyl, cyclopentyl and cyclohexyl.

Each W is independently O or S. Preferably both W are the same. More preferably both W are O.

The term "heteroaryl" refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyridyl, pyridazinyl, pyrimidinyl, pyrazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. A preferred heteroaryl group is pyridine.

The term "heterocyclyl" is defined to include heteroaryl and in addition their unsaturated or partially unsaturated analogues such as 4,5,6,7-tetrahydro-benzothiophenyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

Preferred values of W, $R_1$, $R_2$, $R_3$, $R_4$, $R_5$, $R_6$, $R_7$, $R_8$, $R_9$ and X of the compound of formula I are, in any combination, as set out below:

Both W are O;

$R_1$ is H, trifluoromethyl, cyano, halogen or methyl;

$R_2$ is H, trifluoromethyl, cyano, methoxy, halogen or methyl;

X is $C_1$-$C_6$haloalkyl or cyano;

$R_3$ is H or $C_1$-$C_6$alkyl;

$R_4$, $R_5$, $R_6$ and $R_7$ are independently hydrogen or methyl;

$R_8$ is hydrogen, $C_1$-$C_6$alkyl, $C_1$-$C_6$haloalkyl, $C_2$-$C_6$alkenyl, $C_2$-$C_6$alkynyl, or $R_8$ is $C_1$-$C_6$ alkyl substituted by one or more $C_1$-$C_6$alkoxy, $C_1$-$C_6$alkylthio; and $R_9$ is hydrogen, $C_1$-$C_6$alkyl, $C_1$-$C_6$alkoxy, or halogen.

More preferably, $R_1$ is H or methyl. In particular, $R_1$ is H.

More preferably, $R_2$ is H.

More preferably, X is trifluoromethyl or cyano. In particular, X is trifluoromethyl. In particular, X is cyano.

More preferably, $R_3$ is H.

Preferably $R_8$ is hydrogen, methyl, ethyl, n-propyl or iso-propyl. More preferably, $R_8$ is hydrogen, methyl or ethyl. In particular, $R_8$ is hydrogen or methyl.

More preferably, $R_9$ is H.

In particular, $R_4$, $R_5$, $R_6$ and $R_7$ are H.

Table 1 below includes examples of compounds of formula (I) wherein W is O and $R_1$, $R_2$, $R_3$, $R_4$, $R_5$, $R_6$, $R_7$, $R_8$, $R_9$ and X are as defined.

TABLE 1

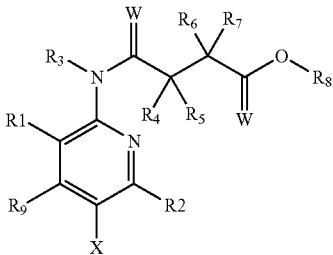

In all compounds listed, W = O

| Compound | X   | R1   | R2  | R3 | R4 | R5 | R6 | R7 | R8  | R9 |
|----------|-----|------|-----|----|----|----|----|----|-----|----|
| 1.00 | CN | H | H | H | H | H | H | H | $CH_3$ | H |
| 1.01 | $CF_3$ | H | H | H | H | H | H | H | $CH_3$ | H |
| 1.02 | CN | H | H | H | H | H | H | H | H | H |
| 1.03 | $CF_3$ | H | H | H | H | H | H | H | H | H |
| 1.04 | CN | $CH_3$ | H | H | H | H | H | H | H | H |
| 1.05 | $CF_3$ | $CH_3$ | H | H | H | H | H | H | H | H |
| 1.06 | CN | $CH_3$ | H | H | H | H | H | H | $CH_3$ | H |
| 1.07 | $CF_3$ | $CH_3$ | H | H | H | H | H | H | $CH_3$ | H |
| 1.08 | CN | Cl | H | H | H | H | H | H | H | H |
| 1.09 | $CF_3$ | Cl | H | H | H | H | H | H | H | H |
| 1.10 | CN | Cl | H | H | H | H | H | H | $CH_3$ | H |
| 1.11 | $CF_3$ | Cl | H | H | H | H | H | H | $CH_3$ | H |
| 1.12 | CN | $OCH_3$ | H | H | H | H | H | H | H | H |
| 1.13 | $CF_3$ | $OCH_3$ | H | H | H | H | H | H | H | H |
| 1.14 | CN | $OCH_3$ | H | H | H | H | H | H | $CH_3$ | H |
| 1.15 | $CF_3$ | $OCH_3$ | H | H | H | H | H | H | $CH_3$ | H |
| 1.16 | CN | H | Cl | H | H | H | H | H | H | H |
| 1.17 | $CF_3$ | H | Cl | H | H | H | H | H | H | H |
| 1.18 | CN | H | Cl | H | H | H | H | H | $CH_3$ | H |
| 1.19 | $CF_3$ | H | Cl | H | H | H | H | H | $CH_3$ | H |
| 1.20 | CN | H | H | H | H | H | H | H | H | Cl |
| 1.21 | $CF_3$ | H | H | H | H | H | H | H | H | Cl |
| 1.22 | CN | H | H | H | H | H | H | H | $CH_3$ | Cl |
| 1.23 | $CF_3$ | H | H | H | H | H | H | H | $CH_3$ | Cl |

The compounds of Formula I according to the invention can be used as plant growth regulators or seed germination promoters by themselves, but they are generally formulated into plant growth regulation or seed germination promotion compositions using formulation adjuvants, such as carriers, solvents and surface-active agents (SFAs). Thus, the present invention further provides a plant growth regulator composition comprising a plant growth regulation compound as described herein and an agriculturally acceptable formulation adjuvant or carrier. The present invention further provides a seed germination promoter composition comprising a seed germination promoter compound as described herein and an agriculturally acceptable formulation adjuvant or carrier. Preferably the composition consists essentially of a compound of Formula I and an agriculturally acceptable formulation adjuvant or carrier. In the alternative, the composition consists of a compound of Formula I and at least one agriculturally acceptable formulation adjuvant or carrier. In one embodiment, the present invention provides a composition comprising a compound of Formula I and an agriculturally acceptable carrier, wherein in Formula I, W is O; $R_1$ is H, trifluoromethyl, cyano, halogen or methyl; $R_2$ is H, methoxy, trifluoromethyl, cyano, halogen or methyl; X is $C_1$-$C_6$haloalkyl or cyano; $R_3$ is H or $C_1$-$C_6$alkyl; $R_4$, $R_5$, $R_6$ and $R_7$ are independently hydrogen or methyl; $R_8$ is hydrogen, $C_1$-$C_6$alkyl, $C_1$-$C_6$haloalkyl, $C_2$-$C_6$ alkenyl, $C_2$-$C_6$alkynyl, or $R_8$ is $C_1$-$C_6$ alkyl substituted by at least one $C_1$-$C_6$alkoxy, $C_1$-$C_6$alkylthio; and $R_9$ is hydrogen.

In a further embodiment, the present invention provides a composition comprising a compound of Formula I and an agriculturally acceptable carrier, wherein in Formula I, W is O; $R_1$ is H or methyl; $R_2$ is H; X is trifluoromethyl or cyano; $R_3$ is H; $R_4$, $R_5$, $R_6$ and $R_7$ are independently hydrogen or methyl; $R_8$ is hydrogen or methyl; and $R_9$ is hydrogen.

The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I) or (I').

Dustable powders (DP) may be prepared by mixing a compound of Formula (I) or (I') with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) or (I') with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) or (I') with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) or (I') and one or more powdered solid diluents or carriers, or from pre-formed blank granules by absorbing a compound of Formula (I) or (I') (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) or (I') in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) or (I') in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) or (I') either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) or (I') is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I) or (I'). SCs may be prepared by ball or bead milling the solid compound of Formula (I) or (I') in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) or (I') may be dry milled and added to water, containing agents hereinbefore described, to produce the desired end product.

Aerosol formulations comprise a compound of Formula (I) or (I') and a suitable propellant (for example n-butane). A compound of Formula (I) or (I') may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) or (I') and, optionally, a carrier or diluent therefor. The polymeric shell may be produced by either an interfacial polycondensation reaction or by a coacervation procedure. The compositions may provide for controlled release of the compound of Formula (I) or (I') and they may be used for seed treatment. A compound of Formula (I) or (I') may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I) or (I'). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I) or (I')).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The present invention still further provides a method for regulating the growth of plants in a locus, wherein the method comprises application to the locus of a plant growth regulating amount of a composition according to the present invention. Preferably the composition is applied by spray application to the leaves of the plant.

The present invention also provides a method for promoting the germination of seeds, comprising applying to the seeds, or to a locus containing seeds, a seed germination promoting amount of a composition according to the present invention.

The application is generally made by spraying the composition, typically by tractor mounted sprayer for large areas, but other methods such as dusting (for powders), drip or drench can also be used. Alternatively the composition may be applied in furrow or directly to a seed before or at the time of planting.

The compound of formula (I) or (I') or composition of the present invention may be applied to a plant, part of the plant, plant organ, plant propagation material or a surrounding area thereof.

In one embodiment, the invention relates to a method of treating a plant propagation material comprising applying to the plant propagation material a composition of the present invention in an amount effective to promote germination and/or regulate plant growth. The invention also relates to a plant propagation material treated with a compound of formula (I) or (I') or a composition of the present invention. Preferably, the plant propagation material is a seed.

The term "plant propagation material" denotes all the generative parts of the plant, such as seeds, which can be used for the multiplication of the latter and vegetative plant materials such as cuttings and tubers. In particular, there may be mentioned the seeds, roots, fruits, tubers, bulbs, and rhizomes.

Methods for applying active ingredients to plant propagation material, especially seeds, are known in the art, and include dressing, coating, pelleting and soaking application methods of the propagation material. The treatment can be applied to the seed at any time between harvest of the seed and sowing of the seed or during the sowing process. The seed may also be primed either before or after the treatment. The compound of formula (I) or (I') may optionally be applied in combination with a controlled release coating or technology so that the compound is released over time.

The composition of the present invention may be applied pre-emergence or post-emergence. Suitably, where the composition is being used to regulate the growth of crop plants, it may be applied pre or post-emergence, but preferably post-emergence of the crop. Where the composition is used to promote the germination of seeds, it may be applied pre-emergence.

The rates of application of compounds of Formula I may vary within wide limits and depend on the nature of the soil, the method of application (pre- or post-emergence; seed dressing; application to the seed furrow; no tillage application etc.), the crop plant, the prevailing climatic conditions, and other factors governed by the method of application, the time of application and the target crop. For foliar or drench application, the compounds of Formula I according to the invention are generally applied at a rate of from 0.001 to 2000 g/ha, especially from 0.001 to 400 g/ha. For seed treatment the rate of application is generally between 0.0005 and 150 g per 100 kg of seed.

Plants in which the composition according to the invention can be used include crops such as cereals (for example wheat, barley, rye, oats); beet (for example sugar beet or fodder beet); fruits (for example pomes, stone fruits or soft fruits, such as apples, pears, plums, peaches, almonds, cherries, strawberries, raspberries or blackberries); leguminous plants (for example beans, lentils, peas or soybeans); oil plants (for example rape, mustard, poppy, olives, sunflowers, coconut, castor oil plants, cocoa beans or groundnuts); cucumber plants (for example marrows, cucumbers or melons); fibre plants (for example cotton, flax, hemp or jute); citrus fruit (for example oranges, lemons, grapefruit or mandarins); vegetables (for example spinach, lettuce, asparagus, cabbages, carrots, onions, tomatoes, potatoes, cucurbits or paprika); lauraceae (for example avocados, cinnamon or camphor); maize; rice; tobacco; nuts; coffee; sugar cane; tea; vines; hops; durian; bananas; natural rubber plants; turf or ornamentals (for example flowers, shrubs, broad-leaved trees or evergreens such as conifers). This list does not represent any limitation.

The invention may also be used to regulate the growth, or promote the germination of seeds of non-crop plants, for example to facilitate weed control by synchronizing germination.

Crops are to be understood as also including those crops which have been modified by conventional methods of breeding or by genetic engineering. For example, the invention may be used in conjunction with crops that have been rendered tolerant to herbicides or classes of herbicides (e.g. ALS-, GS-, EPSPS-, PPO-, ACCase- and HPPD-inhibitors). An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. Methods of rending crop plants tolerant to HPPD-inhibitors are known, for example from WO0246387; for example the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Chenchrus, Lolium, Festuca, Setaria, Eleusine, Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), Nature-Gard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Compounds of the present invention may be in the form of an ester or an acid, either of which may have plant growth regulating properties. As suggested in WO2009/109570, it is thought that the ester form of the compounds of Formula I may be hydrolysed in planta to the acid form. This may be a particular advantage where the esterified compounds are more readily taken up by the plant, for example through leaf tissue.

In a further aspect of the present invention, the compounds or composition of the present invention may be applied in combination with one or more compounds having a pesticidal effect. Such compounds include those that possess fungicidal, herbicidal, safening, plant growth regulation, insecticidal, nematicidal or acaricidal activity.

In a further aspect of the present invention, the compounds or composition of the present invention may be applied in combination with one or more other compounds having a crop enhancement effect. Such compounds include micronutrients, saccharides, amino acids, flavonoids, quinines, and plant activators/growth stimulators. For example, such compounds include natural or synthetic hormones, auxins, brassinosteroids, gibberellins, abscisic acid, cytokinins, jasmonates, strigolactones, salicylic acid, ethylene, 1-methylcyclopropene, trinexapac-ethyl or derivatives thereof. Such compounds also include pesticides that have a crop enhancement effect, for example strobilurins (including azoxystrobin, pyraclostrobin), and neonicotinoids (including thiamethoxam, and imidacloprid).

The compounds of the invention may be made by the following methods.

Compounds of formula (I) or (I') may be prepared from a compound of formula (III) via acylation by reaction of a compounds of formula (II) within Z is halogen such as chlorine and R8 is C1-C6 alkyl, C1-C6 haloalkyl, C1-C6 alkyl substituted by hydroxyl or amine protected or not, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate.

Compounds of formula (II) are commercially available, such as methyl succinate chloride or can be made by methods known to a person skilled in the art.

SCHEME 2

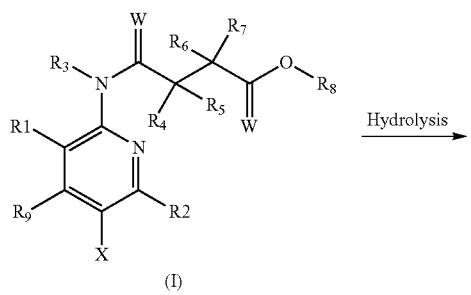

Hydrolysis

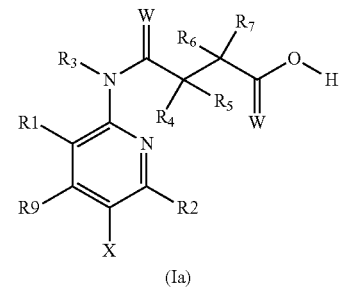

(Ia)

SCHEME 1

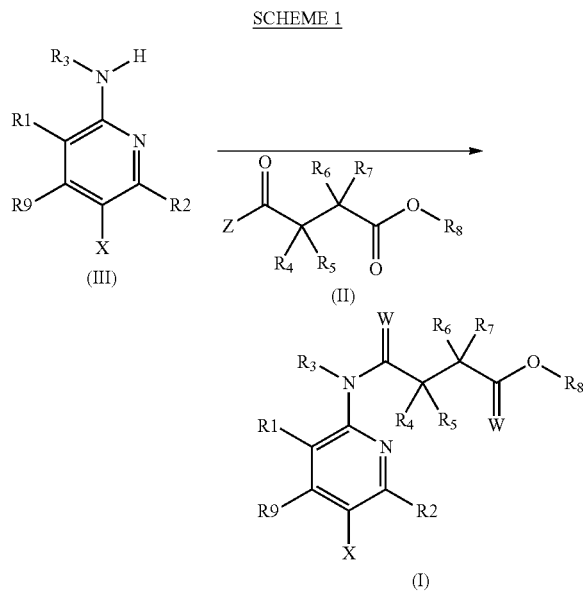

Compounds of formula (Ia) may be made by treatment of compounds of formula (I) or (I'), wherein R8 is C1-C6 alkyl, C1-C6 haloalkyl, C1-C6 alkyl substituted by hydroxyl or amine protected or not, by hydrolysis under standard conditions, such as treatment with an alkali hydroxide, such as sodium hydroxide or potassium hydroxide, in a solvent, such as ethanol or tetrahydrofuran, in the presence of water. Another alternative is the treatment of the ester of formula (Ia) with an acid, such as trifluoroacetic acid, in a solvent, such as dichloromethane, followed by addition of water. The reaction is carried out preferably at a temperature of from −20° C. to +100° C., more preferably from 20° C. to 80° C., in particular at 50° C.

SCHEME 3

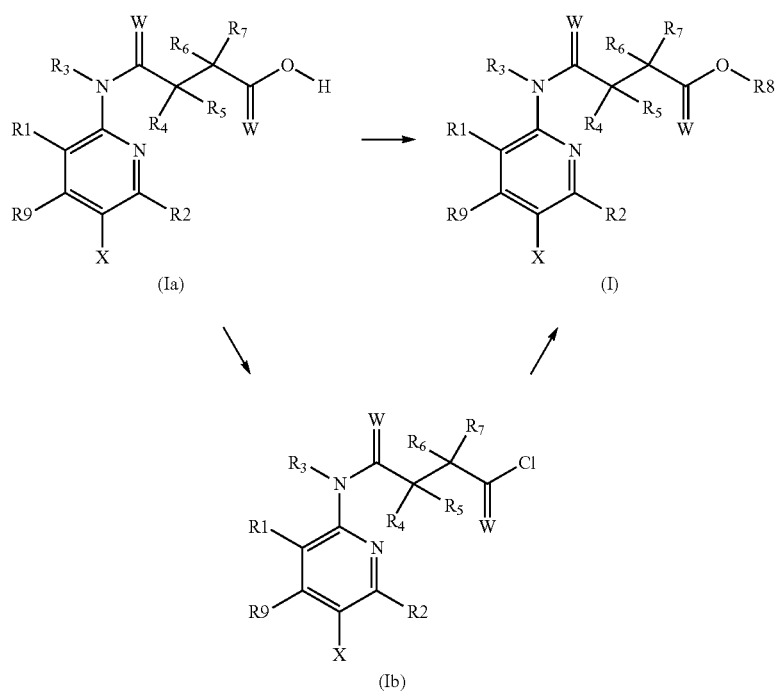

Compounds of formula (I) or (I') may be prepared from a compound of formula (Ia) via acylation by reaction of a alcohol derivative in the presence of a coupling reagent, such as DCC(N,N'-dicyclohexylcarbodiimide), EDC (1-ethyl-3-[3-dimethylamino-propyl]carbodiimide hydrochloride) or BOP-Cl (bis(2-oxo-3-oxazolidinyl)phosphonic chloride), in the presence of a base, such as pyridine, triethylamine, 4-(dimethylamino)pyridine or diisopropylethylamine, and optionally in the presence of a nucleophilic catalyst, such as hydroxybenzotriazole.

Alternatively, Compounds of formula (I) or (I') may be prepared from a compound of formula (Ib) via acylation. The acylation reaction may be carried out under basic conditions (for example in the presence of pyridine, triethylamine, 4-(dimethylamino)pyridine or diisopropylethylamine) and in a suitable solvent, such as, for instance, tetrahydrofuran, optionally in the presence of a nucleophilic catalyst. The reaction is carried out at a temperature of from −120° C. to +130° C., preferably from −100° C. to 100° C. Alternatively, the reaction may be conducted in a biphasic system comprising an organic solvent, preferably ethyl acetate, and an aqueous solvent, preferably a saturated solution of sodium bicarbonate.

Compounds of formula (Ib) may be prepared from a compound of formula (Ia), under standard conditions, such as treatment with thionyl chloride or oxalyl chloride, in a solvent, such as dichloromethane. The reaction is carried out preferably at a temperature of from −20° C. to +100° C., more preferably from 0° C. to 50° C., in particular at ambient temperature.

SCHEME 4

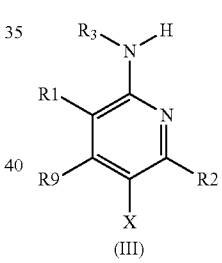

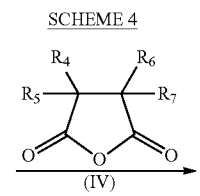

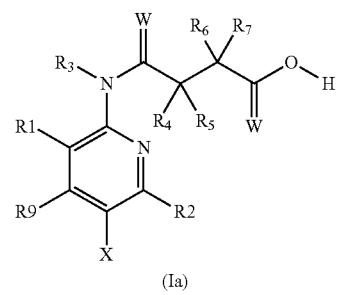

Compounds of formula (Ia) may be made by treatment of compounds of formula (III) by treatment with a anhydride derivatives of formula (IV), such as succinyl anhydride, in a solvent, such as tetrahydrofuran. The reaction is carried out preferably at a temperature from −20° C. to +120° C., more preferably from 20° C. to 120° C.

SCHEME 5:

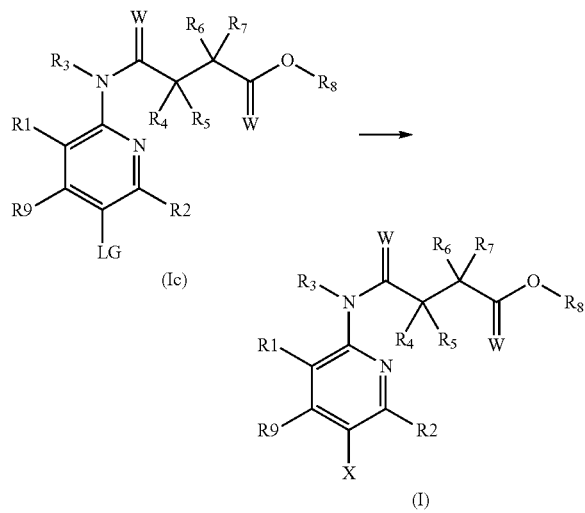

Compounds of Formula (I) or (I') wherein X is aryl, heteroaryl or $C_3$-$C_8$cycloalkyl derivatives such as thiophen, vinyl, allyl or cyclopropyl can be prepared by the reaction of compounds of formula (Ic) wherein LG is a suitable leaving group, such as, for example halogen or triflate with a derivative of formula Z—X, wherein Z is a boron or a tin derivatives and X is as described for the compound of Formula (I) or (I') in the presence of a suitable catalyst/ligand system, often a palladium (0) complex and in the presence or not of a base such as potassium carbonate. These reactions can be carried out or not under microwave irradiation. These reactions being known to the person skilled in the art under the name of Stille, Suzuki coupling, see for example: Strategic Applications of Named Reactions in Organic Synthesis Kurti, Laszlo; Czako, Barbara; Editors. USA. (2005), Publisher: Elsevier Academic Press, Burlington, Mass. p. 448 (Suzuki coupling) and p. 438 (Stille coupling) and cited references.

SCHEME 6:

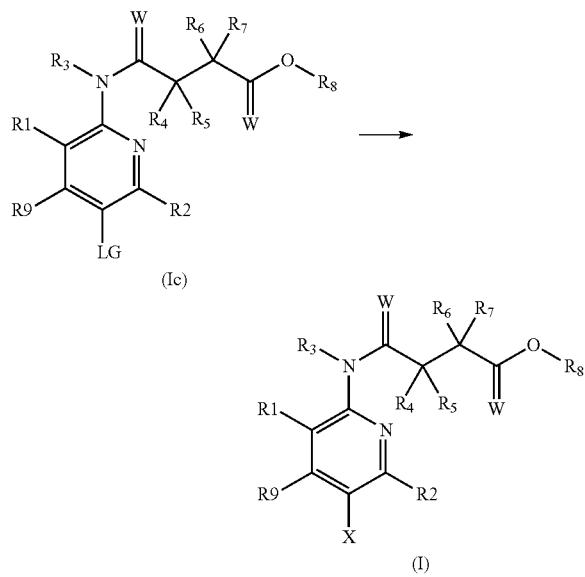

Compounds of Formula (I) or (I') wherein X is CCR where R is an $C_1$-$C_6$ alkyl, H or trialkyl silyl can be prepared by the reaction of compounds of formula (Ic) wherein LG is a suitable leaving group such as for example halogen or triflate with a derivative of formula HCCR in the presence of a suitable catalyst/ligand system, often a palladium (0) complex with or without a source of copper such as copper iodide and an organic base such as diisopropylethyl amine. This reaction being known to the person skilled in the art under the name of Sonogashira coupling, see for example: Strategic Applications of Named Reactions in Organic Synthesis Kurti, Laszlo; Czako, Barbara; Editors. USA. (2005), Publisher: Elsevier Academic Press, Burlington, Mass. p. 424 (Sonogashira coupling) and cited references. Compounds of Formula (I) or (I') wherein X is CCH can be prepared by the reaction of compounds of formula (I) or (I') wherein X is $CCSiR_3$ where R is a C1-C6 alkyl group by reaction with a base such as potassium carbonate of a fluoride source such as potassium fluoride.

Compounds of formula (I) or (I'), wherein W is sulfur, may be prepared from a compound of formula (I) or (I'), wherein W is oxygen, by treatment with a thio-transfer reagent, such as Lawesson's reagent or phosphorus pentasulfide.

EXAMPLES

The following HPLC-MS methods were used for the analysis of the compounds:

Method A:
Spectra were recorded on a ZQ Mass Spectrometer from Waters (Single quadrupole mass spectrometer) equipped with an electrospray source (Polarity: positive or negative ions, Capillary: 3.00 kV, Cone: 30.00 V, Extractor: 2.00 V, Source Temperature: 100° C., Desolvation Temperature: 250° C., Cone Gas Flow: 50 L/Hr, Desolvation Gas Flow: 400 L/Hr, Mass range: 100 to 900 Da) and an Agilent 1100 LC (Solvent degasser, binary pump, heated column compartment and diode-array detector. Column: Phenomenex Gemini C18, 3 µm, 30×3 mm, Temp: 60° C., DAD Wavelength range (nm): 210 to 500, Solvent Gradient: A=water+0.05% HCOOH, B=Acetonitrile/Methanol (4:1, v:v)+0.04% HCOOH: gradient: 0 min 5% B; 2-2.8 min 100% B; 2.9-3 min 5%. Flow (ml/min) 1.7

Method B:
Spectra were recorded on a ZQ Mass Spectrometer from Waters (Single quadrupole mass spectrometer) equipped with an electrospray source (Polarity: positive or negative ions, Capillary: 3.00 kV, Cone: 30.00 V, Extractor: 2.00 V, Source Temperature: 100° C., Desolvation Temperature: 250° C., Cone Gas Flow: 50 L/Hr, Desolvation Gas Flow: 400 L/Hr, Mass range: 100 to 900 Da) and an Agilent 1100 LC (Solvent degasser, binary pump, heated column compartment and diode-array detector. Column: Phenomenex Gemini C18, 3 µm, 30×3 mm, Temp: 60° C., DAD Wavelength range (nm): 210 to 500, Solvent Gradient: A=water+5% MeOH+0.05% HCOOH, B=Acetonitrile+0.05% HCOOH: gradient: 0 min 0% B; 2-2.8 min 100% B; 2.9-3 min 0%. Flow (ml/min) 1.7

Method C:
Spectra were recorded on a ZQ Mass Spectrometer from Waters (Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 50 L/Hr, Desolvation Gas Flow: 400 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: 0 min 10% B, 90% A; 1.2-1.5 min 100% B; Flow (ml/min) 0.85

Method D:
Spectra were recorded on a SQD Mass Spectrometer from Waters (Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 250° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Phenomenex Gemini C18, 3 μm, 30×2 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85

Method E:
Same conditions that used for Method C except that the spectrometer is: SQD Mass Spectrometer from Waters (Single quadrupole mass spectrometer)

Method F:
Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85

The following abbreviations are used throughout this section: s=singlet; bs=broad singlet; d=doublet; dd=double doublet; dt=double triplet; t=triplet; tt=triple triplet, q=quartet; m=multiplet; Me=methyl; Et=ethyl; Pr=propyl; Bu=butyl; M.p.=melting point; RT=retention time, M+H$^+$=molecular cation (i.e. measured molecular weight).

Synthesis of Intermediate

Example I

Preparation of 6-amino-5-methoxy-pyridine-3-carbonitrile

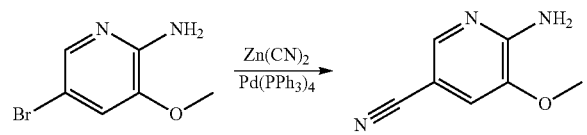

To a solution of 5-bromo-3-methoxy-pyridin-2-amine (3.00 g, 14.8 mmol) in N,N-dimethylformamide (55 mL) under a nitrogen atmosphere was added zinc (II) cyanide (2.78 g, 23.6 mmol) and tetrakis(triphenylphosphine)palladium(0) (2.06 g, 1.77 mmol). The reaction mixture was stirred at 100° C. for 4 h. The reaction mixture was diluted with ethyl acetate and washed successively with a saturated solution of ammonium hydroxide and brine. The phases were separated. The organic phases was dried over sodium sulfate and concentrated. The residue was purified by column chromatography on silica gel (eluent: ethyl acetate/cyclohexane 1:5) to give 6-amino-5-methoxy-pyridine-3-carbonitrile (1.2 g, 54% yield). $^1$H NMR (400 MHz, CDCl$_3$): 7.99 (s, 1H), 6.99 (s, 1H), 3.88 (s, 3H) ppm. $^{13}$C NMR (100 MHz, CDCl$_3$): 152.83, 144.58, 141.27, 118.32, 115.52, 97.66, 55.65. LC-MS (Method B): RT 0.69, 150 (M+H$^+$)

The following Compounds were prepared by the same method using commercial or described starting aminopyridine:

6-amino-5-(trifluoromethyl)pyridine-3-carbonitrile (commercially available too): starting material for A42

Example II methyl 4-[(5-cyano-2-pyridyl)amino]-4-oxo-butanoate A1

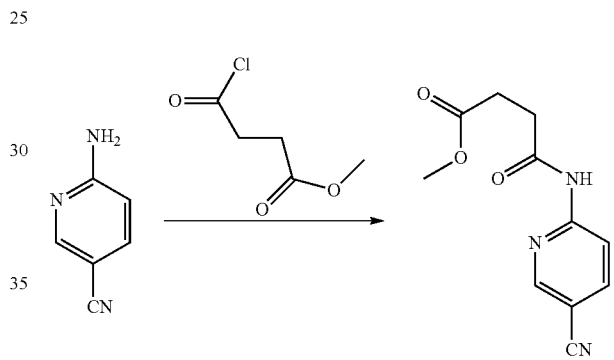

The 6-amino-3-pyridinecarbonitrile (commercially available, 0.470 g, 1.0 eq.) was dissolved in tetrahydrofuran (10 mL) then N,N-dimethylaniline (0.5 mL, 1.0 eq.) and methyl-4-chloro-4-oxo-butanoate (0.54 mL, 1.1 eq.) were successively added. The mixture was reflux for 12 h. The reaction was stopped and the solution was partitioned between ethyl acetate and water. The aqueous layer was separated and extracted with ethyl acetate (2×). The combined organic layer was dried on magnesium sulfate and concentrated under vacuum. The residue was purified by flash chromatography eluting with cyclohexane-ethyl acetate to give methyl 4-[(5-cyano-2-pyridyl)amino]-4-oxo-butanoate A1 (71%). M.p.=161-164° C. $^1$H NMR (400 MHz, DMSO-d6) δ 8.78 (s, 1H), 8.20 (m, 2H), 3.58 (s, 3H), 2.74 (t, 2H), 2.61 (t, 2H) ppm. LC-MS (Method B): RT 1.19, 234 (M+H$^+$)

The following compounds from table A or B were prepared by the same method using commercial or described starting aminopyridine:

Methyl 4-[(3-cyano-5-iodo-2-pyridyl)amino]-4-oxo-butanoate A3

Methyl 4-[(3-bromo-5-chloro-2-pyridyl)amino]-4-oxo-butanoate A5

Methyl 4-[(5-bromo-3-methoxy-2-pyridyl)amino]-4-oxo-butanoate A6

Methyl 4-[(5-cyano-3-methoxy-2-pyridyl)amino]-4-oxo-butanoate A7

Methyl 4-[(5-bromo-3-chloro-2-pyridyl)amino]-4-oxo-butanoate A8

Methyl 4-[(5-cyano-4,6-dimethyl-2-pyridyl)amino]-4-oxo-butanoate A9

Methyl 4-[(3-chloro-5-cyano-2-pyridyl)amino]-4-oxo-butanoate A10

Methyl 4-[(3,5-dichloro-2-pyridyl)amino]-4-oxo-butanoate A11

Methyl 4-oxo-4-[(3,5,6-trichloro-2-pyridyl)amino]butanoate A12

Ethyl 4-[(5-cyano-2-pyridyl)amino]-4-oxo-butanoate was synthesised by the same method after replacement of the methyl-4-chloro-4-oxo-butanoate by ethyl 4-chloro-4-oxo-butanoate A22

Methyl 4-oxo-4-[[5-[1,2,2,2-tetrafluoro-1-(trifluoromethyl)ethyl]-2-pyridyl]amino]butanoate A24

Methyl 4-[(5-bromo-6-methoxy-2-pyridyl)amino]-4-oxo-butanoate A26

Methyl 4-[(5-methylsulfanyl-2-pyridyl)amino]-4-oxo-butanoate A29

Methyl 4-[(5-methoxy-2-pyridyl)amino]-4-oxo-butanoate A30

Methyl 4-[(5-chloro-4-ethoxy-2-pyridyl)amino]-4-oxo-butanoate A31

Methyl 4-[(5-acetyl-2-pyridyl)amino]-4-oxo-butanoate A33

Methyl 4-[(5-cyano-6-methyl-2-pyridyl)amino]-4-oxo-butanoate A35

Methyl 4-[(5-cyano-2-pyridyl)amino]-2,2-dimethyl-4-oxo-butanoate B1 using as reagent the commercial 2,2'-dimethylsuccinic methyl ester after generation of the acid chloride analogue with oxalyl chloride and a drop of DMF.

Methyl 6-[(4-methoxy-4-oxo-butanoyl)amino]pyridine-3-carboxylate A37

Methyl 4-[(5-bromo-4-ethoxy-2-pyridyl)amino]-4-oxo-butanoate A38

Methyl 4-[[5-cyano-3-(trifluoromethyl)-2-pyridyl]amino]-4-oxo-butanoate A42

Methyl 4-[[5-bromo-3-(trifluoromethyl)-2-pyridyl]amino]-4-oxo-butanoate A44

Methyl 4-[[3-chloro-5-(trifluoromethyl)-2-pyridyl]amino]-4-oxo-butanoate A46

Methyl 4-[(5-cyano-3-methyl-2-pyridyl)amino]-4-oxo-butanoate A48

Methyl 4-[(5-bromo-6-chloro-2-pyridyl)amino]-4-oxo-butanoate A49

Methyl 4-[(5-nitro-2-pyridyl)amino]-4-oxo-butanoate A55

Methyl 4-[(5-methylsulfonyl-2-pyridyl)amino]-4-oxo-butanoate A56

Methyl 4-[(5-chloro-4-methoxy-2-pyridyl)amino]-4-oxo-butanoate A57

Methyl 4-[(5-chloro-6-methoxy-2-pyridyl)amino]-4-oxo-butanoate A58

Methyl 4-[(5-bromo-4-methoxy-2-pyridyl)amino]-4-oxo-butanoate A59

Methyl 4-oxo-4-[[5-(1,1,2,2,2-pentafluoroethyl)-2-pyridyl]amino]butanoate A60 using as starting material the 5-(1,1,2,2,2-pentafluoroethyl)pyridin-2-amine (Example X)

Methyl 4-[(5-formyl-2-pyridyl)amino]-4-oxo-butanoate A76

Example III

4-[(5-cyano-2-pyridyl)amino]-4-oxo-butanoic acid A2

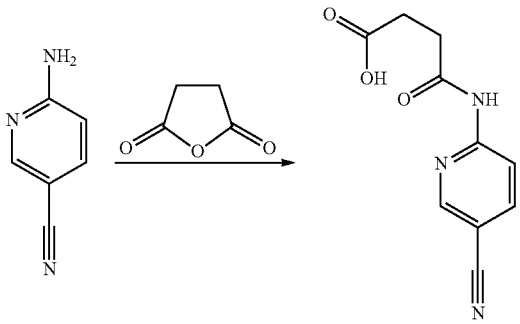

The 6-amino-3-pyridinecarbonitrile (commercially available, 1.0 g, 8.40 mmol) was dissolved in tetrahydrofuran (20 mL) then succinic anhydride (1.04 g, 10.5 mmol) was added, the mixture was stirred at 100° C. for 12 h. The reaction was stopped and the solution was washed with a saturated solution of sodium carbonate. The organic layer was concentrated under vacuum. The residue was purified by flash chromatography eluting with methanol-ethyl acetate (5/95) to give 4-[(5-cyano-2-pyridyl)amino]-4-oxo-butanoic acid A2 (0.325 g, 18%). M.p.=220-221° C., $^1$H NMR (400 MHz, DMSO-d6) δ 12.18 (bs, 1H), 11.04 (s, 1H), 8.78 (s, 1H), 8.21 (m, 2H), 2.69 (t, 2H), 2.52 (m, 2H) ppm. LC-MS (Method B): RT 1.00, 218 (M−H$^+$)

The following compounds from table A were prepared by the same method:

4-[(5-bromo-3-chloro-2-pyridyl)amino]-4-oxo-butanoic acid A13

4-[(5-cyano-4,6-dimethyl-2-pyridyl)amino]-4-oxo-butanoic acid A14

4-[(5-cyano-3-methoxy-2-pyridyl)amino]-4-oxo-butanoic acid A15

4-oxo-4-[[5-(trifluoromethyl)-2-pyridyl]amino]butanoic acid A19

4-[(5-bromo-6-methyl-2-pyridyl)amino]-4-oxo-butanoic acid A21

4-[(5-bromo-3-methoxy-2-pyridyl)amino]-4-oxo-butanoic acid A43

4-[[5-bromo-3-(trifluoromethyl)-2-pyridyl]amino]-4-oxo-butanoic acid A45

4-[[3-chloro-5-(trifluoromethyl)-2-pyridyl]amino]-4-oxo-butanoic acid A47

Example IV

4-[(3-cyano-5-iodo-2-pyridyl)amino]-4-oxo-butanoic acid A4

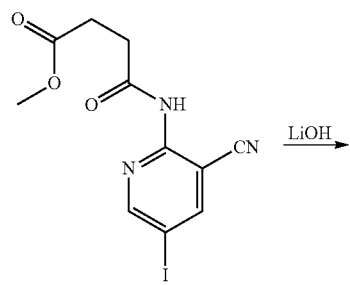

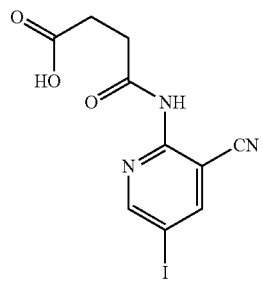

Lithium hydroxide (0.058 g, 1.0 eq.) was added at ambient temperature to a solution of methyl 4-[(3-cyano-5-iodo-2-pyridyl)amino]-4-oxo-butanoate (Example I, A3, 0.500 g, 1.0 eq.) in a mixture of tetrahydrofuran (15 ml) and water (5 mL). The reaction mixture was stirred at room temperature for 3 h. The residue was diluted with a saturated solution of sodium hydrogenocarbonate and washed with ethyl acetate. The aqueous phase was acidified by addition of aqueous hydrochloric acid (concentrated) and extracted two times with ethyl acetate. The combined organic layer was dried on magnesium sulfate and concentrated under vacuum to give the desired compound A4 (23.4%). M.p.=215-218° C., $^1$H NMR (400 MHz, DMSO-d6) δ 12.22 (bs, 1H), 10.98 (s, 1H), 8.96 (s, 1H), 8.77 (s, 1H), 2.72 (t, 2H), 2.55 (m, 2H) ppm. LC-MS (Method A): RT 1.08, 344 (M–H$^+$)

The following compounds from table A or B were prepared by the same method:
4-oxo-4-[(3,5,6-trichloro-2-pyridyl)amino]butanoic acid A16
4-[(3,5-dichloro-2-pyridyl)amino]-4-oxo-butanoic acid A17
4-[(3-bromo-5-chloro-2-pyridyl)amino]-4-oxo-butanoic acid A18
4-oxo-4-[[5-[1,2,2,2-tetrafluoro-1-(trifluoromethyl)ethyl]-2-pyridyl]amino]butanoic acid A25
4-[(5-bromo-6-methoxy-2-pyridyl)amino]-4-oxo-butanoic acid A27
4-[(5-methylsulfanyl-2-pyridyl)amino]-4-oxo-butanoic acid A28
4-[(5-chloro-4-ethoxy-2-pyridyl)amino]-4-oxo-butanoic acid A32
4-[(5-cyano-6-methyl-2-pyridyl)amino]-4-oxo-butanoic acid A36
4-[(5-cyano-2-pyridyl)amino]-2,2-dimethyl-4-oxo-butanoic acid B2
4-[(5-bromo-4-ethoxy-2-pyridyl)amino]-4-oxo-butanoic acid A39
4-[(5-bromo-6-chloro-2-pyridyl)amino]-4-oxo-butanoic acid A50
4-[(5-chloro-4-methoxy-2-pyridyl)amino]-4-oxo-butanoic acid A61
4-[(5-chloro-6-methoxy-2-pyridyl)amino]-4-oxo-butanoic acid A62
4-[(5-bromo-4-methoxy-2-pyridyl)amino]-4-oxo-butanoic acid A63
4-oxo-4-[[5-(1,1,2,2,2-pentafluoroethyl)-2-pyridyl]amino]butanoic acid A64

Example V

Methyl 4-oxo-4-[[5-(trifluoromethyl)-2-pyridyl]amino]butanoate A20

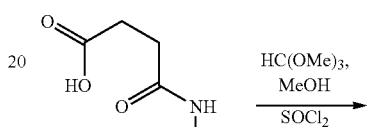

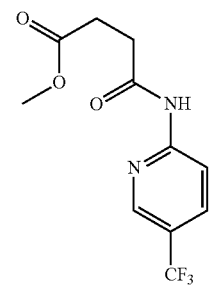

4-Oxo-4-[[5-(trifluoromethyl)-2-pyridyl]amino]butanoic acid (Example 11, A19, 50 mg, 0.19 mmol) and trimethyl orthoformate (60.7 mg, 3 eq.) were dissolved in methanol (4 mL), and thionyl chloride (68.1 mg, 3 eq.) was added dropwise. The reaction was stirred at room temperature for 3 h. The solvent were evaporated and the crude was treated with Dowex 1×8 OH to give the methyl 4-oxo-4-[[5-(trifluoromethyl)-2-pyridyl]amino]butanoate A20 (36 mg, 69%). $^1$H NMR (400 MHz, CDCl$_3$): 2.77 (s, 4H), 3.73 (s, 3H), 7.91 (dd, 1H), 8.33 (d, 1H), 8.54 (s, 1H), 8.59 (s, 1H).

Example VI

Benzyl 4-[(5-cyano-2-pyridyl)amino]-4-oxo-butanoate A23

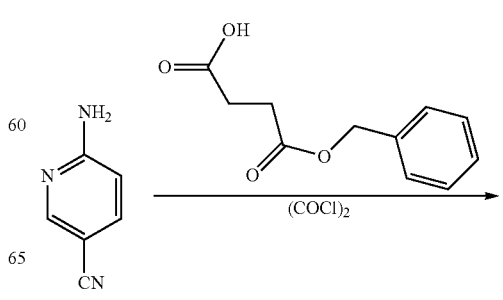

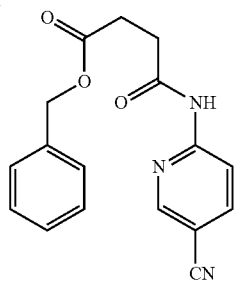

4-Benzyloxy-4-oxo-butanoic acid (commercially available, 2.097 g, 10.1 mmol, 1.2 eq.) was dissolved in dichloromethane then oxalyl dichloride (2.13 g, 1.4 mL, 16.8 mmol, 2.0 eq.) and one drop of N,N-dimethylformamide were added. The solution was stirred at room temperature for 1 h and then refluxed for 1 h. The solvent was removed and dry by vacuum. The residue was dissolved in 30 ml of tetrahydrofuran and was added in a mixture with 6-aminopyridine-3-carbonitrile (commercially available, 1.00 g, 8.39 mmol, 1.0 eq.) in tetrahydrofuran (30 mL) and pyridine (1.99 g, 2.03 mL, 25.2 mmol, 3.0 eq.). The solution was refluxed for 4 h. The reaction was stopped and the solution was partitioned between ethyl acetate and water. The aqueous layer was separated and extracted with ethyl acetate (2×). The combined organic layer was dried on magnesium sulfate and concentrated under vacuum. The residue was purified by flash chromatography eluting with cyclohexane-ethyl acetate (3/1) to give benzyl 4-[(5-cyano-2-pyridyl)amino]-4-oxo-butanoate A23 (2.49 g, 96%). LC-MS (Method A): RT 1.58, 310 (M−H⁺), 308 (M−H⁺).

Example VII benzyl 4-oxo-4-[[5-(trifluoromethyl)-2-pyridyl]amino]butanoate (compound A34)

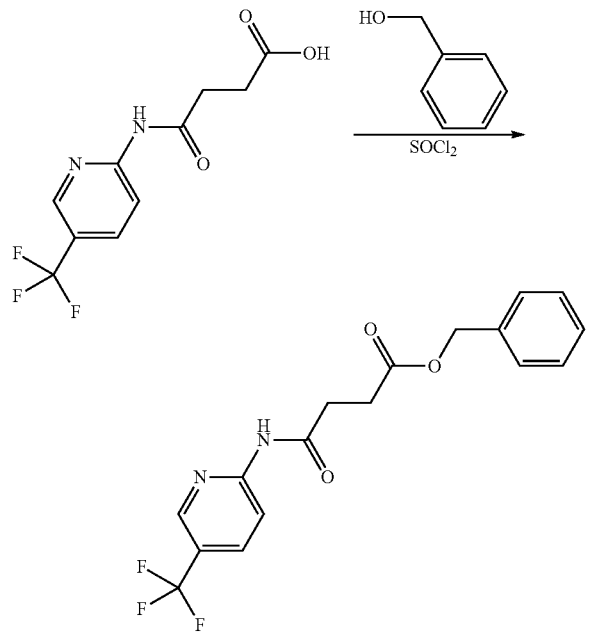

To a solution of phenylmethanol (3 mL) was added dropwise thionyl chloride (3 equiv., 2.29 mmol, 0.169 mL). After 5 min, 4-oxo-4-[[5-(trifluoromethyl)-2-pyridyl]amino]butanoic acid A19 (prepared as described before, 201 mg, 0.766 mmol) was added to the solution. The reaction mixture was stirred overnight at room temperature. The reaction was stopped and the solution was partitioned between ethyl acetate and a saturated solution of sodium hydrogenocarbonate. The aqueous layer was separated and extracted with ethyl acetate (2×). The combined organic layer was washed with water (×2) and brine, dried on magnesium sulfate and concentrated under vacuum. To remove the benzyl alcohol, water was added until the ester precipitated. The ester was filtrated and then washed with water and cyclohexane (20 mL). The residue was first dissolved in ethyl acetate then precipitated with cyclohexane and the solid obtained was filtered to give benzyl 4-oxo-4-[[5-(trifluoromethyl)-2-pyridyl]amino]butanoate A34 (32%). ¹H NMR (400 MHz, CDCl₃) 8.7 (s, 1H), 8.31 (m, 1H), 8.22 (bs, 1H), 7.90 (m, 1H), 7.35 (m, 5H), 5.15 (s, 2H), 2.78 (m, 4H) ppm.

Compound A51, A52, A53, A54, A73, A74, A78, A79, A80 and A81 from table A were prepared by the same method using the corresponding alcohol.

Example VIII

Methyl 4-oxo-4-[(5-vinyl-2-pyridyl)amino]butanoate (compound A40)

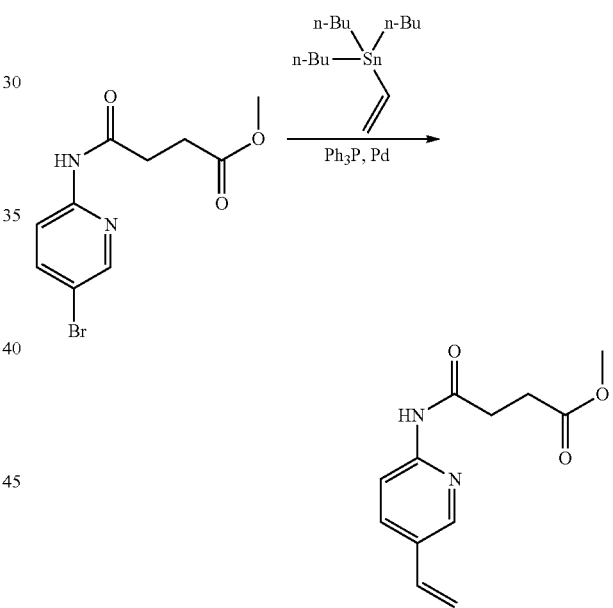

To a solution of methyl 4-[(5-bromo-2-pyridyl)amino]-4-oxo-butanoate (commercially available: 0.25 g, 0.871 mmol) in toluene (10 mL) was added palladium; triphenylphosphane (0.101 g, 0.0871 mmol) and tributyl(vinyl)stannane (0.33 g, 0.30 mL, 1.04 mmol). The reaction mixture was refluxed overnight. Then, 0.05 eq of palladium triphenylphosphane and 0.6 eq of tritutylvinylstannane were added. Volatiles were removed under vacuum and residue taken up in acetonitrile. The acetonitrile phase was washed twice with hexane and concentrated under vacuum. The residue was purified by flash chromatography eluting with cyclohexane-ethyl acetate (3/1) to give methyl 4-oxo-4-[(5-vinyl-2-pyridyl)amino]butanoate (compound A40) (0.20 g, 15%). ¹H NMR (400 MHz, CDCl₃) 8.26 (s, 1H), 8.19 (sb, 1H), 8.15 (m, 2H), 7.76 (m, 1H), 6.65 (m, 1H), 5.34 (d, 1H), 5.30 (d, 1H), 3.72 (s, 3H), 2.75 (m, 4H) ppm.

Example IX

Methyl 4-[(5-ethynyl-2-pyridyl)amino]-4-oxo-butanoate (compound A41)

Step 1: Methyl 4-oxo-4-[[5-(2-trimethylsilylethynyl)-2-pyridyl]amino]butanoate

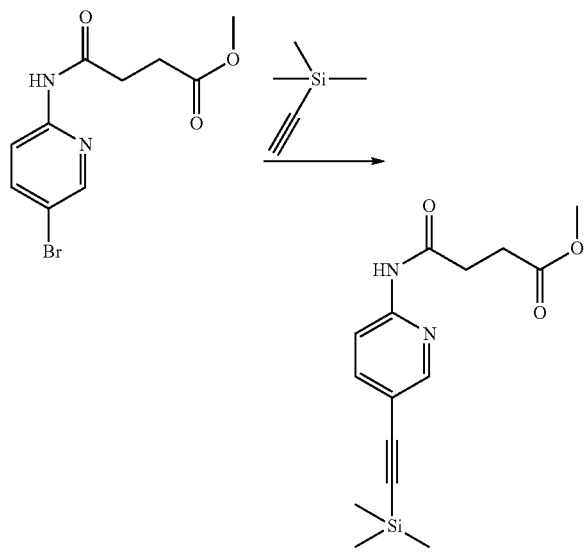

To a solution of methyl 4-[(5-bromo-2-pyridyl)amino]-4-oxo-butanoate (commercially available: 0.25 g, 0.871 mmol) in tetrahydrofuran was added bis(triphenylphosphine) palladium(II) dichloride (61.7536 mg, 0.087 mmol), copper(I) iodide (16.6 mg, 0.087 mmol), triethylamine (889 mg, 1.23 mL, 8.70 mmol) and ethynyltrimethylsilane (130 mg, 0.19 mL, 1.30 mmol). The reaction mixture was stirred at 65° C. overnight. The reaction was stopped and the solution was partitioned between ethyl acetate and water. The aqueous layer was separated and extracted with ethyl acetate (2×). The combined organic layer was dried on magnesium sulfate and concentrated under vacuum. The residue was purified by flash chromatography eluting with cyclohexane-ethyl acetate (3/1) to give methyl 4-oxo-4-[[5-(2-trimethylsilylethynyl)-2-pyridyl]amino]butanoate (26 mg, 10% yield). $^1$H NMR (400 MHz, CDCl$_3$) 8.39 (s, 1H), 8.14 (m, 2H), 7.74 (d, 1H), 3.72 (s, 3H), 2.74 (m, 4H), 0.24 (s, 9H) ppm.

Step 2: Methyl 4-[(5-ethynyl-2-pyridyl)amino]-4-oxo-butanoate A41

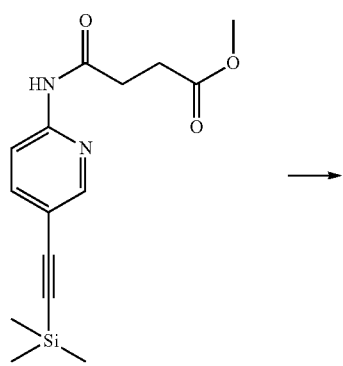

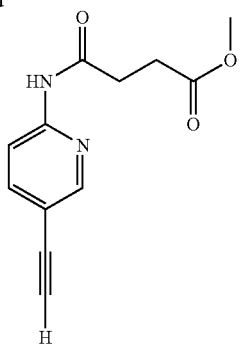

To a solution of methyl 4-oxo-4-[[5-(2-trimethylsilylethynyl)-2-pyridyl]amino]butanoate (26 mg, 0.085 mmol) in methanol, potassium carbonate (5.90 mg, 0.042 mmol) is added in one portion and the reaction mixture is stirred at room temperature for 2 h. The reaction was stopped and the solution was partitioned between ethyl acetate and water. The aqueous layer was separated and extracted with ethyl acetate (2×). The combined organic layer was dried on magnesium sulfate and concentrated under vacuum to give methyl 4-[(5-ethynyl-2-pyridyl)amino]-4-oxo-butanoate A41 (12 mg, 60% yield). $^1$H NMR (400 MHz, CDCl$_3$) 8.39 (d, 1H), 8.16 (m, 2H), 7.77 (d, 1H), 3.72 (s, 3H), 2.74 (m, 4H) ppm.

Example X 5-(1,1,2,2,2-pentafluoroethyl)pyridin-2-amine

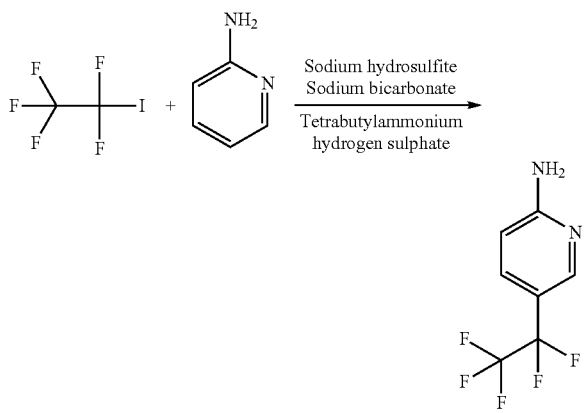

To a solution of 2-aminopyridine (25.0 g, 263 mmol) in a mixture of water (250 ml) and tert-butyl methyl ether (25 ml) was added, successively perfluoroethyl iodide (80 g, 38 ml, 315 mmol), sodium hydrosulfite (64.6 g, 26 ml, 315 mmol), sodium hydrogen carbonate (26.5 g, 315.6 mmol) and tetrabutyl ammonium hydrogen sulfate ("TBAHS") (0.11 equiv., 9.92 g, 28.9 mmol). The reaction mixture was stirred at ambient temperature for 16 h. The mixture was filtered and the filtrate was extracted twice with tert-butyl methyl ether. The combined organic phases were washed successively with water, aqueous hydrochloric acid (1N) and brine, dried over sodium sulfate and concentrated. The residue was purified by flash chromatography (AcOEt/cyclohexane) to give 5-(1,1,2,2,2-pentafluoroethyl)pyridin-2-amine in 7% yield. $^1$H NMR (400 MHz, CDCl$_3$) 8.23 (d, 1H), 7.61 (d, 1H), 6.72 (m, 1H), 5.04 (sb, 2H, NH₂) ppm. The major by-product was 3,5-bis (1,1,2,2,2-pentafluoroethyl)pyridin-2-amine.

Example XI

Methyl 4-oxo-4-[[5-(1H-tetrazol-5-yl)-2-pyridyl]amino]butanoate A65

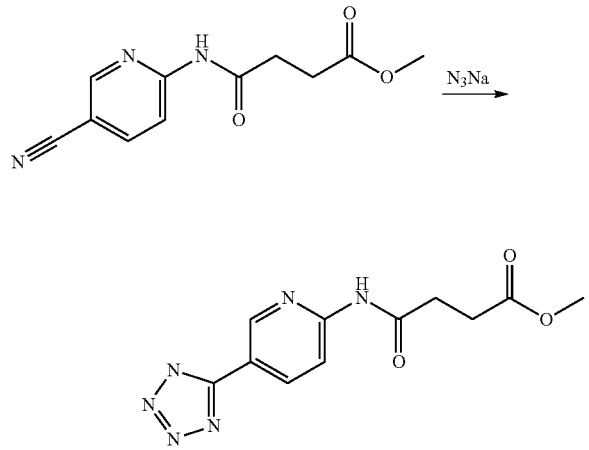

A mixture of methyl 4-[(5-cyano-2-pyridyl)amino]-4-oxo-butanoate A1 (0.200 g, 0.857 mmol), sodium azide (0.169 g, 0.09 ml, 2.57 mmol) and triethylammonium chloride (0.187 g, 0.17 ml, 1.33 mmol) was stirred 4 h at 150° C. in 1-methyl-2-pyrrolidinone (10 mL).

The mixture was cooled down and diluted with water. After acidification with aqueous hydrochloric acid (1N), the filtrate was extracted twice with ethyl acetate. The organic phases were combined, dried over sodium sulfate and concentrated. The residue was suspended in ethyl acetate and filtered to give methyl 4-oxo-4-[[5-(1H-tetrazol-5-yl)-2-pyridyl]amino]butanoate A65 (0.06 g, 25% yield). M.p.: 246-248° C., LC-MS (Method F) RT 0.53, 277 (M+H⁺).

Example XII

Butyl 4-[(5-cyano-2-pyridyl)amino]-4-oxo-butanoate A66

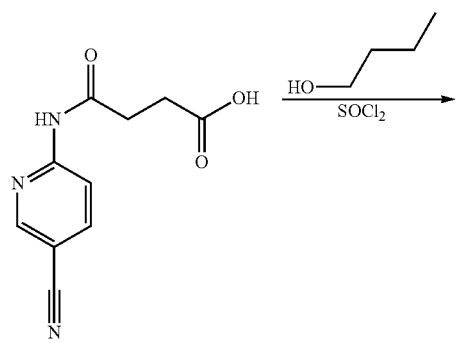

-continued

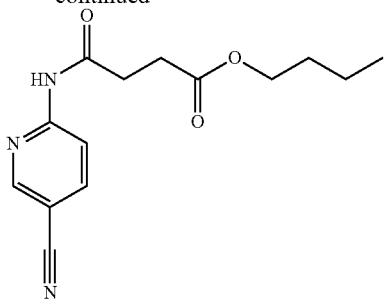

To a solution of butan-1-ol (3 mL) was added dropwise thionyl chloride (2.73 mmol, 0.200 mL 3 eq). After 5 min, 4-[(5-cyano-2-pyridyl)amino]-4-oxo-butanoic acid A2 (prepared as described before, 200 mg, 0.912 mmol) was added to the solution. The reaction mixture was stirred overnight at room temperature. The reaction was stopped and the solution was partitioned between ethyl acetate and water. The aqueous layer was separated and extracted with ethyl acetate (2×). The combined organic layer was washed with a saturated solution of sodium hydrogenocarbonete and dried on magnesium sulfate, then concentrated under vacuum. The residue was first washed with cyclohexane and the solid obtained was purified by flash chromatography eluting with cyclohexane-ethyl acetate to give butyl 4-[(5-cyano-2-pyridyl)amino]-4-oxo-butanoate A66 (10%) and the by-product butyl 6-[(4-butoxy-4-oxo-butanoyl)amino]pyridine-3-carboxylate A67 (9%).

Butyl 4-[(5-cyano-2-pyridyl)amino]-4-oxo-butanoate A66; LC-MS (Method F) RT 0.89, 276 (M+H⁺).

Butyl 6-[(4-butoxy-4-oxo-butanoyl)amino]pyridine-3-carboxylate A67; LC-MS (Method F) RT 01.10, 351 (M+H⁺).

Example XIII

Methyl 4-[(5-cyano-2-pyridyl)-methyl-amino]-4-oxo-butanoate A68

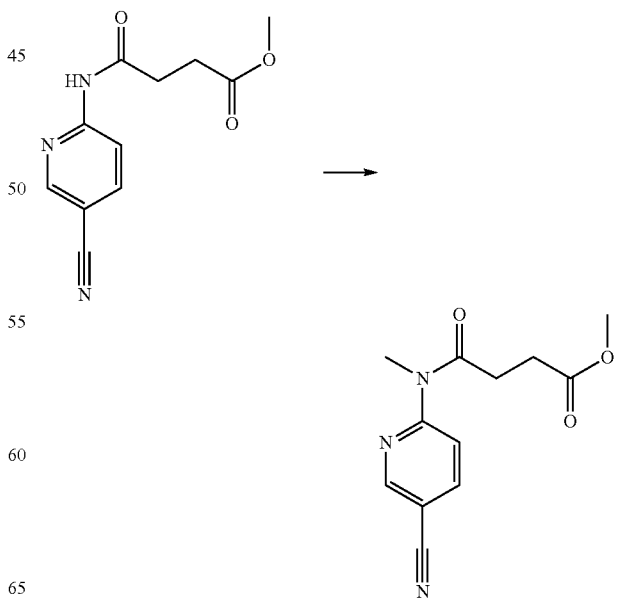

To a solution of 4-[(5-cyano-2-pyridyl)amino]-4-oxo-butanoic acid A2 (prepared as described before, 200 mg, 0.857 mmol, 1 equiv.) in acetonitrile (5 mL) was added iodomethane (10 equiv., 8.57 mmol, 0.534 mL) and sodium hydride (1 equiv., 0.857 mmol, 0.037 mL). The reaction mixture was stirred overnight at room temperature. The next day 1 equiv. sodium hydride (34.3 mg) was added to increase the amount of product and the mixture was stirred for 1 h at room temperature. The reaction was stopped and the solution was partitioned between ethyl acetate and water. The aqueous layer was separated and extracted with ethyl acetate (2×). The combined organic layer was dried on magnesium sulfate, and then concentrated under vacuum. The solid obtained was purified by flash chromatography eluting with cyclohexane-ethyl acetate and then dissolved in ethyl acetate and precipitated with cyclohexane. After cooling with ice/water, the precipitated solid was filtrated and give methyl 4-[(5-cyano-2-pyridyl)-methyl-amino]-4-oxo-butanoate A68 (45%). $^1$H NMR (400 MHz, CDCl$_3$) 8.69 (s, 1H), 7.90 (m, 2H), 3.71 (s, 3H), 3.52 (s, 3H), 2.92 (m, 2H), 2.71 (m, 2H) ppm.

Compound A69 from table A were prepared by the same method using the corresponding alkylating agent.

Example XIV

Methyl 4-[[5-(difluoromethyl)-2-pyridyl]amino]-4-oxo-butanoate A77

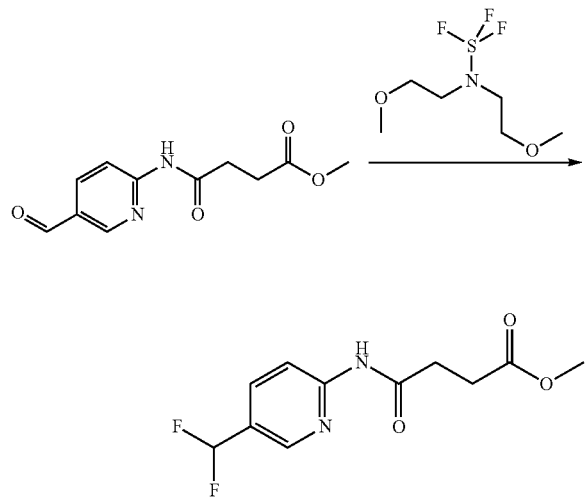

A suspension of methyl 4-[(5-formyl-2-pyridyl)amino]-4-oxo-butanoate A76 (0.09 g, 0.381 mmol, 1 equiv.) in toluene (6 mL) was heated at 80° C. in presence of deoxo-fluor (50 mass %) in toluene (0.50576 g, 1.1430 mmol, 3 equiv.) overnight. The reaction was stopped and the solution was partitioned between ethyl acetate and water. The aqueous layer was separated and extracted with ethyl acetate (2×). The combined organic layer was dried on magnesium sulfate, and then concentrated under vacuum. The solid obtained was purified by flash chromatography (FC) eluting with a gradient of cyclohexane-ethyl acetate to give methyl 4-[[5-(difluoromethyl)-2-pyridyl]amino]-4-oxo-butanoate A77 (52%). LC-MS (Method F) RT 0.71, 259 (M+H$^+$).

Example XV

Methyl 4-oxo-4-[[5-(2-thienyl)-2-pyridyl]amino]butanoate A71 and 4-oxo-4-[[5-(2-thienyl)-2-pyridyl]amino]butanoic acid A72

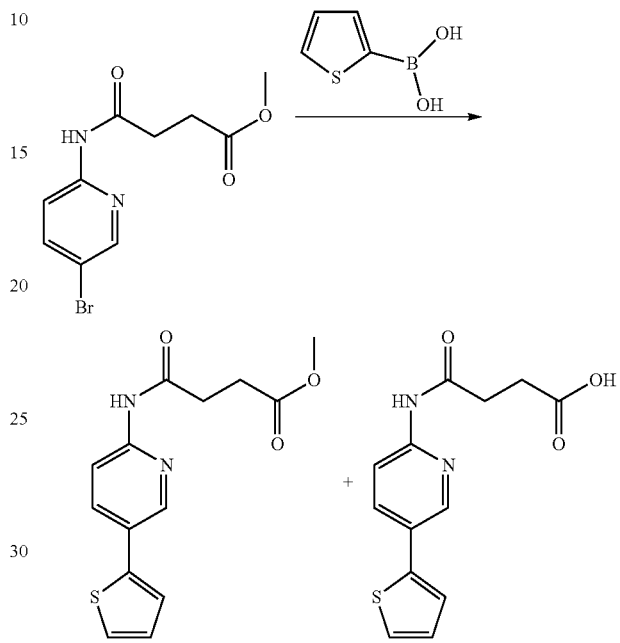

In a microwave tube was charged with methyl 4-[(5-bromo-2-pyridyl)amino]-4-oxo-butanoate (commercially available or prepared as described in example II using as starting material the commercially available: 5-bromo-2-aminopyridine; 200 mg, 0.696 mmol, 1 equiv.), 2-thienylboronic acid (3 equiv., 2.09 mmol, 3 equiv.), bis(tri-tert-butylphosphine)palladium(0) (22 mg, 0.043 mmol, 0.06 equiv.), potassium carbonate (179 mg, 1.28 mmol, 1.8 equiv.) and dissolved in glycol dimethyl ether (5 ml)/water (2 ml). The reaction mixture was heated at 130° C. for 20 minutes in the microwave. The reaction was stopped and the solution was partitioned between ethyl acetate and alkaline water. The aqueous layer was separated and extracted with ethyl acetate (2×). The combined organic layer was dried on magnesium sulfate, and then concentrated under vacuum. The solid obtained was purified by flash chromatography (RF-machine) eluting with a gradient of cyclohexane-ethyl acetate to give methyl 4-oxo-4-[[5-(2-thienyl)-2-pyridyl]amino]butanoate A71 (8%). %). LC-MS (Method F) RT 0.85, 291 (M+H$^+$). The aqueous layer was acidified with hydrogen chloride until pH 1-2 and extracted with ethyl acetate (2×). The combined organic layer was dried on magnesium sulfate, and then concentrated under vacuum. The solid was washed with ethyl acetate, filtered and dried to give 4-oxo-4-[[5-(2-thienyl)-2-pyridyl]amino]butanoic acid A72 (31% yield). %). LC-MS (Method F) RT 0.74, 277 (M+H$^+$).

Example XVI

Methyl 4-[[5-(5-methyl-1,2,4-oxadiazol-3-yl)-2-pyridyl]amino]-4-oxo-butanoate A75

Step 1: Methyl 4-[[5-[(Z)—N'-hydroxycarbamimidoyl]-2-pyridyl]amino]-4-oxo-butanoate

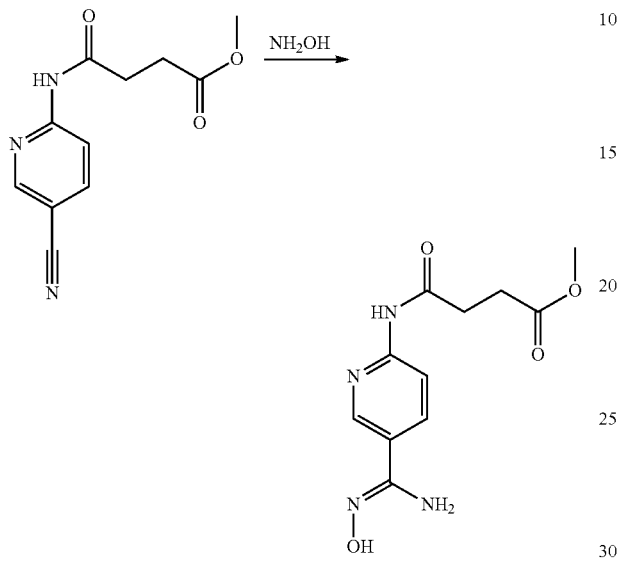

A solution of sodium bicarbonate (1.81 g, 21.4 mmol, 5 equiv.) and hydroxylamine hydrochloride (1.50 g, 21.4 mmol, 5 equiv.) in water (12 mL) was added to an solution of 4-[(5-cyano-2-pyridyl)amino]-4-oxo-butanoic acid A2 (1.00 g, 4.29 mmol, 1 equiv.) in methanol (120 mL) at 80° C. The solution was heated at 80° C. overnight, before being concentrated under vacuum. The residue was partitioned between ethyl acetate (50 mL) and water (50 mL). The aqueous layer was separated and extracted with ethyl acetate (3×50 ml). The combined organic layer was dried on magnesium sulfate, and then concentrated under vacuum to give 760 mg of crude product. This crude product was adsorbed over isolute before purification by flash chromatography eluted with a gradient of methanol and dichloromethane (0 to 10% in methanol) to give methyl 4-[[5-[(Z)—N'-hydroxycarbamimidoyl]-2-pyridyl]amino]-4-oxo-butanoate (0.46 g, 1.73 mmol, 40% yield).

Step 2: methyl 4-[[5-[(Z)—N'-acetoxycarbamimidoyl]-2-pyridyl]amino]-4-oxo-butanoate

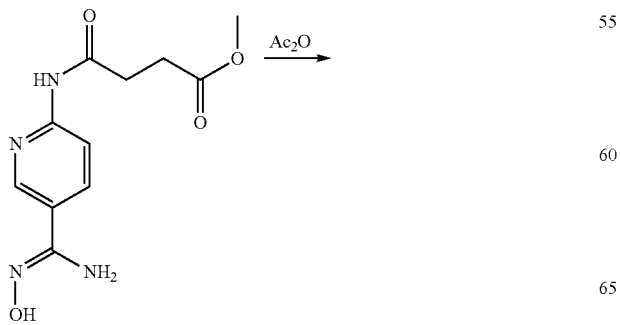

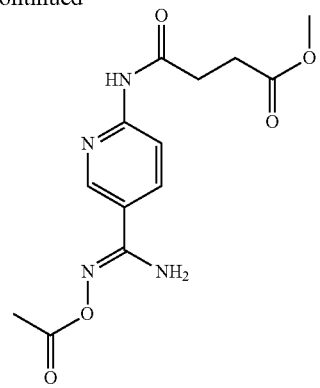

To a suspension of methyl 4-[[5-[(Z)—N'-hydroxycarbamimidoyl]-2-pyridyl]amino]-4-oxo-butanoate (obtained as described in step 1, 0.15 g, 0.56 mmol, 1 equiv.) in dichloromethane (30 mL) was added acetic anhydride (1.98 mL, 20.3 mmol, 36 equiv.). The mixture was stirred for 5 days, before concentration under vacuum giving methyl 4-[[5-[(Z)—N'-acetoxycarbamimidoyl]-2-pyridyl]amino]-4-oxo-butanoate which is used in the next step without extra purification.

Step 3: Methyl 4-[[5-(5-methyl-1,2,4-oxadiazol-3-yl)-2-pyridyl]amino]-4-oxo-butanoate A75

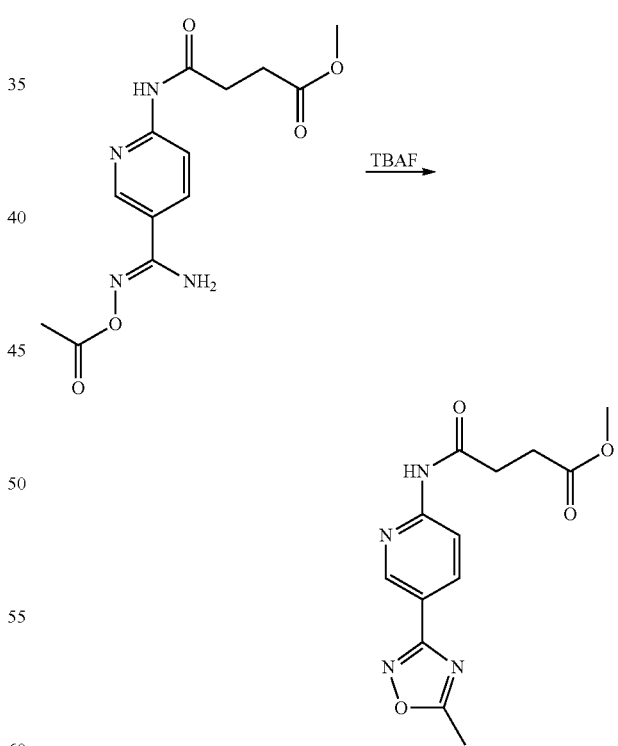

To a solution of methyl 4-[[5-[(Z)—N'-acetoxycarbamimidoyl]-2-pyridyl]amino]-4-oxo-butanoate (obtained in step 2, 0.18 g, 0.58 mmol, 1 equiv.) in tetrahydrofuran (20 mL) was added tetrabutylammonium fluoride (1.0 mol/L) in THF (0.053 g, 0.058 mL, 0.058 mmol, 0.1 equiv.) at room temperature. The mixture was stirred for 4 h at room temperature.

The residue was partitioned between ethyl acetate and water. The aqueous layer was separated and extracted with ethyl acetate (3×50 ml). The combined organic layer was dried on magnesium sulfate, and then concentrated under vacuum. The residue was purified by flash chromatography, eluted with a gradient of ethyl acetate and cyclohexane to give methyl 4-[[5-(5-methyl-1,2,4-oxadiazol-3-yl)-2-pyridyl]amino]-4-oxo-butanoate A75 (0.062 g, 37% yield). LC-MS (Method F) RT 0.72, 291 (M+H$^+$).

Example XVII

Methyl 4-oxo-4-[[5-(3-pyridyl)-2-pyridyl]amino]butanoate A82

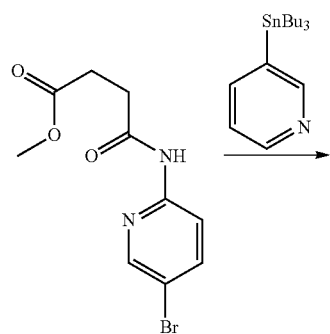

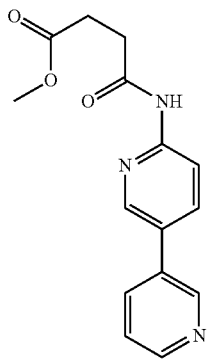

Methyl 4-[(5-bromo-2-pyridyl)amino]-4-oxo-butanoate (Commercially available or prepared as described in example II using as starting material the commercially available: 5-bromo-2-aminopyridine, 200 mg, 0.697 mmol) was dissolved in toluene in a microwave vial and 3-pyridyltributylstannane (0.836 mmol, 0.290 mL) and tetrakis(triphenylphosphine) palladium(0) (0.069 mmol) were added. Argon was bubbling through the mixture for ca. 5 min and the vial was heated under microwave irradiations for 10 min at 150° C. The solvent was evaporated and the residue was diluted with acetonitrile, washed with cyclohexane (2×) and evaporated. The product was purified by flash chromatography (RF-machine, AcOEt/cyclohexane: 0/100→100/0) to give methyl 4-oxo-4-[[5-(3-pyridyl)-2-pyridyl]amino]butanoate (compound A82) (0.051 g, 26% Yield). LC-MS (Method F) RT 0.50, 286 (M+H$^+$).

Compound A83, A84 and A85 from table A were prepared by the same method using the corresponding coupling reagent.

TABLE A

Compounds of formula (I) wherein R4, R5, R6 and R7 are H and both W are oxygen

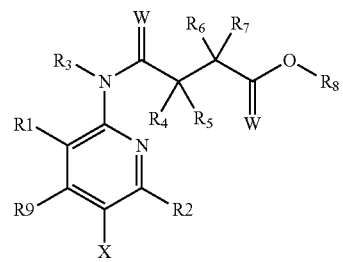

(I)

| Compound | X | R1 | R2 | R3 | R8 | R9 | LCMS method | RT (min.) | Mass |
|---|---|---|---|---|---|---|---|---|---|
| A1 | CN | H | H | H | CH$_3$ | H | A | 1.19 | 234 (M + H$^+$) |
| A2 | CN | H | H | H | H | H | B | 1.00 | 218 (M − H$^+$) |
| A3 | I | CN | H | H | CH$_3$ | H | A | 1.27 | 360 (M + H$^+$) |
| A4 | I | CN | H | H | H | H | A | 1.08 | 344 (M − H$^+$) |
| A5 | Cl | Br | H | H | CH$_3$ | H | A | 1.30 | 321 (M − H$^+$) |
| A6 | Br | MeO | H | H | CH$_3$ | H | A | 1.26 | 319 (M + H$^+$) |
| A7 | CN | MeO | H | H | CH$_3$ | H | B | 1.15 | 264 (M + H$^+$) |
| A8 | Br | Cl | H | H | CH$_3$ | H | B | 1.33 | 323 (M + H$^+$) |

TABLE A-continued

Compounds of formula (I) wherein R4, R5, R6 and R7 are H and both W are oxygen

| Compound | X | R1 | R2 | R3 | R8 | R9 | LCMS method | RT (min.) | Mass |
|---|---|---|---|---|---|---|---|---|---|
| A9 | CN | H | $CH_3$ | H | $CH_3$ | $CH_3$ | B | 1.41 | 262 (M + H$^+$) |
| A10 | CN | Cl | H | H | $CH_3$ | H | B | 1.15 | 268 (M + H$^+$) |
| A11 | Cl | Cl | H | H | $CH_3$ | H | A | 1.29 | 275 (M − H$^+$) |
| A12 | Cl | Cl | Cl | H | $CH_3$ | H | A | 1.52 | 311 (M − H$^+$) |
| A13 | Br | Cl | H | H | H | H | B | 1.15 | 307 (M + H$^+$) 305 (M − H$^+$) |
| A14 | CN | H | $CH_3$ | H | H | $CH_3$ | B | 1.24 | 248 (M + H$^+$) 246 (M − H$^+$) |
| A15 | CN | MeO | H | H | H | H | B | 0.96 | 250 (M + H$^+$) 248 (M − H$^+$) |
| A16 | Cl | Cl | Cl | H | H | H | A | 1.34 | 297 (M − H$^+$) |
| A17 | Cl | Cl | H | H | H | H | A | 1.12 | 261 (M − H$^+$) |
| A18 | Cl | Br | H | H | H | H | A | 1.13 | 307 (M + H$^+$) |
| A19 | $CF_3$ | H | H | H | H | H | $^1$H NMR (400 MHz, DMSO-d6): 2.52 (t, 3H), 2.68 (t, 3H), 8.15 (dd, 1H), 8.25 (d, 1H), 8.69 (s, 1H), 10.98 (s, 1H), 12.17 (br s, 1H) | | |
| A20 | $CF_3$ | H | H | H | $CH_3$ | H | $^1$H NMR (400 MHz, CDCl$_3$): 2.77 (s, 4H), 3.73 (s, 3H), 7.91 (dd, 1H), 8.33 (d, 1H), 8.54 (s, 1H), 8.59 (s, 1H) | | |
| A21 | Br | H | $CH_3$ | H | H | H | $^1$H NMR (400 MHz, DMSO-d6): 2.47-2.50 (m, 5H), 2.61 (t, 2H), 7.84 (d, 1H), 7.92 (d, 1H), 10.63 (s, 1H), 12.11 (br s, 1H) | | |
| A22 | CN | H | H | H | Ethyl | H | A | 1.31 | 248 (M + H$^+$) 246 (M − H$^+$) |
| A23 | CN | H | H | H | Benzyl | H | A | 1.58 | 310 (M + H$^+$) 308 (M − H$^+$) |
| A24 | C3F7 | H | H | H | $CH_3$ | H | F | 1.58 | 377 (M + H$^+$) |
| A25 | C3F7 | H | H | H | H | H | F | 0.89 | 363 (M + H$^+$) |
| A26 | Br | H | $OCH_3$ | H | $CH_3$ | H | F | 0.87 | 319 (M + H$^+$) |
| A27 | Br | H | $OCH_3$ | H | H | H | F | 0.76 | 305 (M + H$^+$) |
| A28 | $SCH_3$ | H | H | H | H | H | F | 0.59 | 241 (M + H$^+$) |

TABLE A-continued

Compounds of formula (I) wherein R4, R5, R6 and R7 are H and both W are oxygen

| Compound | X | R1 | R2 | R3 | R8 | R9 | LCMS method | RT (min.) | Mass |
|---|---|---|---|---|---|---|---|---|---|
| A29 | SCH$_3$ | H | H | H | CH$_3$ | H | F | 0.71 | 255 (M + H$^+$) |
| A30 | OCH$_3$ | H | H | H | CH$_3$ | H | Mp ° C. 140° C. | | |
| A31 | Cl | H | H | H | CH$_3$ | OEt | F | 0.84 | 287 (M + H$^+$) |
| A32 | Cl | H | H | H | H | OEt | F | 0.72 | 273 (M + H+) 271 (M − H+) |
| A33 | CH$_3$C(O) | H | H | H | CH$_3$ | H | F | 0.61 | 251 (M + H$^+$) |
| A34 | CF$_3$ | H | H | H | OCH$_2$Ph | H | F | 1.00 | 353 (M + H$^+$) |
| A35 | CN | H | CH$_3$ | H | CH$_3$ | H | F | 0.70 | 248 (M + H$^+$) |
| A36 | CN | H | CH$_3$ | H | H | H | Mp ° C. 191° C. | | |
| A37 | CO$_2$CH$_3$ | H | H | H | CH$_3$ | H | $^1$H NMR (400 MHz, CDCl$_3$): 8.90 (s, 1H), 8.28 (m, 2H), 3.93 (s, 3H), 3.73 (s, 3H), 2.74 (m, 4H) ppm | | |
| A38 | Br | H | H | H | CH$_3$ | OEt | D | 0.81 | 333 (M + H$^+$) 331 (M − H$^+$) |
| A39 | Br | H | H | H | H | OEt | B | 1.39 | 317 (M + H$^+$) |
| A40 | H$_2$CCH | H | H | H | CH$_3$ | H | B | 1.27 | 235 (M + H$^+$) |
| A41 | HCC | H | H | H | CH$_3$ | H | B | 1.31 | 233 (M + H$^+$) |
| A42 | CN | CF$_3$ | H | H | CH$_3$ | H | B | 1.24 | 302 (M + H$^+$), 300 (M +− H$^+$) |
| A43 | Br | H | H | H | H | OCH$_3$ | B | 1.11 | 305 (M + H$^+$), 303 (M − H$^+$) |
| A44 | Br | CF$_3$ | H | H | CH$_3$ | H | B | 1.39 | 357 (M + H$^+$) |
| A45 | Br | CF$_3$ | H | H | H | H | B | 1.23 | 341 (M + H$^+$) |
| A46 | CF$_3$ | Cl | H | H | CH$_3$ | H | B | 1.42 | 311 (M + H$^+$) |
| A47 | CF$_3$ | Cl | H | H | H | H | B | 1.30 | 297 (M + H$^+$) |
| A48 | CN | CH3 | H | H | CH$_3$ | H | B | 1.09 | 248 (M + H+) 246 (M − H+) |
| A49 | Br | H | H | H | CH$_3$ | Cl | B | 1.59 | 323 (M + H$^+$) 321 (M − H$^+$) |
| A50 | Br | H | H | H | H | Cl | B | 1.45 | 309 (M + H$^+$) |

TABLE A-continued

Compounds of formula (I) wherein R4, R5, R6 and R7 are H and both W are oxygen

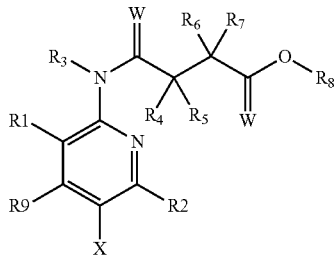

(I)

| Compound | X | R1 | R2 | R3 | R8 | R9 | LCMS method | RT (min.) | Analytical data: LCMS, Mp °C. or $^1$H NMR Mass |
|---|---|---|---|---|---|---|---|---|---|
| A51 | CF$_3$ | H | H | H | —CH$_2$C(H)CH$_2$ | H | D | 0.88 | 303 (M + H$^+$) 301 (M − H$^+$) |
| A52 | CF$_3$ | H | H | H | —CH$_2$CH$_2$OCH$_3$ | H | D | 0.79 | 321 (M + H$^+$), 319 (M − H$^+$) |
| A53 | CF$_3$ | H | H | H | —(CH$_2$)$_2$C(H)CH$_2$ | H | B | 1.73 | 317 (M + H$^+$) |
| A54 | CF$_3$ | H | H | H | CH$_2$CF$_3$ | H | D | 0.92 | 345 (M + H$^+$) |
| A55 | NO$_2$ | H | H | H | H | H | B | 1.29 | 254 (M + H$^+$), 252 (M − H$^+$) |
| A56 | SO$_2$CH$_3$ | H | H | H | CH$_3$ | H | F | 0.55 | 287 (M + H$^+$) |
| A57 | Cl | H | H | H | CH$_3$ | OCH$_3$ | F | 0.76 | 273 (M + H$^+$) |
| A58 | Cl | H | OCH$_3$ | H | CH$_3$ | H | F | 0.86 | 273 (M + H$^+$) |
| A59 | Br | H | H | H | CH$_3$ | OCH$_3$ | F | 0.78 | 319 (M + H$^+$) |
| A60 | CF$_3$CF$_2$ | H | H | H | CH$_3$ | H | F | 0.73 | 327 (M + H$^+$) |
| A61 | Cl | H | H | H | H | OCH$_3$ | F | 0.64 | 259 (M + H$^+$) |
| A62 | Cl | H | OCH$_3$ | H | H | H | F | 0.74 | 259 (M + H$^+$) |
| A63 | Br | H | H | H | H | OCH$_3$ | F | 0.66 | 303 (M + H$^+$) |
| A64 | CF3CF2 | H | H | H | H | H | F | 0.61 | 313 (M + H$^+$) |
| A65 | tetrazol-5-yl | H | H | H | CH$_3$ | H | F | 0.53 | 277 (M + H$^+$) |
| A66 | CN | H | H | H | Bu | H | F | 0.89 | 276 (M + H$^+$) |
| A67 | C(O)OBu | H | H | H | Bu | H | F | 1.10 | 351 (M + H$^+$) |
| A68 | CN | H | H | CH$_3$ | CH$_3$ | H | | | $^1$H NMR (400 MHz, CDCl$_3$): 8.69 (s, 1H), 7.90 (m, 2H), 3.71 (s, 3H), 3.52 (s, 3H), 2.92 (m, 2H), 2.71 (m, 2H). |
| A69 | CN | H | H | CH$_3$CH$_2$ | CH$_3$ | H | | | $^1$H NMR (400 MHz, CDCl$_3$): 8.71 (s, 1H), 7.92 (m, 1H), 7.78 (m, 1H), 4.05 (q, 2H), 3.70 (s, 3H), 2.85 (m, 2H), 2.2.72 (m, 2H), 2.38 (t, 3H). |
| A70 | CN | H | H | H | iPr | H | F | 0.80 | 220 (M + H$^+$) |
| A71 | Thiophen-2-yl | H | H | H | CH$_3$ | H | F | 0.85 | 291 (M + H$^+$) |
| A72 | Thiophen-2-yl | H | H | H | H | H | F | 0.74 | 277 (M + H$^+$) |
| A73 | CF$_3$ | H | H | H | Bu | H | F | 1.02 | 319 (M + H$^+$) |

TABLE A-continued

Compounds of formula (I) wherein R4, R5, R6 and R7 are H and both W are oxygen

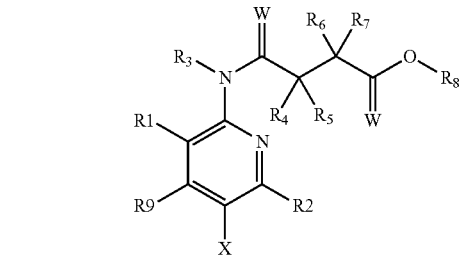

(I)

| Compound | X | R1 | R2 | R3 | R8 | R9 | LCMS method | RT (min.) | Mass |
|---|---|---|---|---|---|---|---|---|---|
| A74 | CF3 | H | H | H | cyclopentyl | H | F | 1.03 | 331 (M + H$^+$) |
| A75 | 5-methyl-1,2,4-oxadiazol-3-yl | H | H | H | CH$_3$ | H | F | 0.72 | 291 (M + H$^+$) |
| A76 | C(O)H | H | H | H | CH$_3$ | H | F | 0.58 | 237 (M + H$^+$) |
| A77 | CHF2 | H | H | H | CH$_3$ | H | F | 0.71 | 259 (M + H$^+$) |
| A78 | CF3 | H | H | H | CH$_2$CCH | H | F | 0.89 | 301 (M + H$^+$) |
| A79 | CF3 | H | H | H | (CH$_2$)$_2$SCH$_3$ | H | F | 0.94 | 337 (M + H$^+$) |
| A80 | CF3 | H | H | H | CH$_2$CHCl$_2$ | H | F | 1.00 | 359 (M + H$^+$) |
| A81 | CF3 | H | H | H | CH(CH$_3$)$_2$ | H | F | 0.99 | 317 (M + H$^+$) |
| A82 | Pyridn-3-yl | H | H | H | CH$_3$ | H | F | 0.50 | 286 (M + H$^+$) |
| A83 | 2-Furyl | H | H | H | CH$_3$ | H | F | 0.80 | 275 (M + H$^+$) |
| A84 | 3-methyl-pyridin-2-yl | H | H | H | CH$_3$ | H | F | 0.64 | 300 (M + H$^+$) |
| A85 | 2-methyl-sulfanyl-pyrimidin-4-yl | H | H | H | CH$_3$ | H | F | 0.83 | 303 (M + H$^+$) |

TABLE B

Compounds of formula (I) wherein R1, R2, R3 and R9 are H and both W are oxygen (I)

| Compound | X | R4 | R5 | R6 | R7 | R8 | Mp ° C. | | |
|---|---|---|---|---|---|---|---|---|---|
| B1 | CN | H | H | CH$_3$ | CH$_3$ | CH$_3$ | 129 | | |

| Compound | X | R4 | R5 | R6 | R7 | R8 | LCMS method | RT (min.) | Mass |
|---|---|---|---|---|---|---|---|---|---|
| B2 | CN | H | H | CH$_3$ | CH$_3$ | H | F | 0.64 | 248 (M + H$^+$) |

BIOLOGICAL EXAMPLES

Two bioassays were developed in order to assay the activity of the compounds of the present invention. In the first assay, the activity of the compound was quantified in beans based on its effect on the elongation of the petiole of the second leaf. In the second assay, the compound's effect on the root growth of wheat was determined.

Example B1

Bean Assay

French beans (*Phaseolus vulgaris*) of the variety *Fulvio* were sown in 0.5 liters pots in a sandy loam without additional fertilizer. Plants grew under greenhouse conditions at 22/18° C. (day/night) and 80% relative humidity; light was supplemented above 25 kLux.

Plants were treated with test compounds eleven days after sowing, when the second internode was 2-5 mm long. Before application, the compounds were each dissolved in dimethyl sulfoxide and diluted in a mixture of lanolin-oil and acetone (1:2 ratio by volume). Five micro liters of the test compound was pipetted to the wound that was created after abscising the bract leaf from the base of the second internode. Fourteen days after application, the length of the petiole of the second leaf (measured from the base of the petiole to the base of the first leaflet) was determined in order to quantify the activity of the compounds.
The following compounds gave at least an increase of 10% of the length of the petiole of the second leaf:
A19, A2, A1, A4, A23, A31, A32, A38, A39, A52, A54, B2.

Example B2

Wheat Assay

The test compounds were dissolved in small volumes of dimethyl sulfoxide and diluted to the appropriate concentration with water. Wheat (*Triticum aestivum*) seeds of the variety *Arina* were sown in mini-pouches (10.5×9.0 cm) containing 5 mL of the appropriate compound solution. The mini pouches were stored at 17° C. for three days to enable the seeds to germinate. Plants were then stored at 5° C. Twelve days after sowing/application, plants were removed from the mini-pouches and scanned. The effect of the compounds was quantified by determining plant (root and shoot) area and curliness of the roots (curliness is an indicator of brassinosteroid-type activity).
The following compounds gave at least a reduction of 15% of the plant (root and shoot) area and showed a curly root phenotype:
A19, A2, A1, A22, A31, A32, A38, A39, A52, A54.

The invention claimed is:
1. A compound of formula (I)

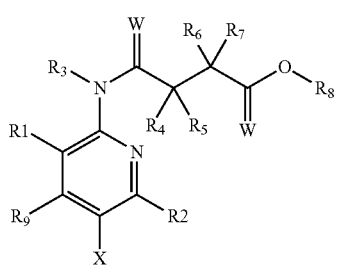

(I)

wherein
each W is O;
$R_1$, $R_2$ and $R_9$ are independently H, $C_1$-$C_6$haloalkyl, $C_1$-$C_6$alkoxy, cyano, halogen, or $C_1$-$C_6$alkyl;
X is halogen, $C_1$-$C_6$haloalkyl, cyano, $C_1$-$C_6$alkoxy, amine, or $C_1$-$C_6$alkylcarbonyl;
and provided that when X is halogen, $R_2$, $R_3$, $R_4$, $R_5$, $R_6$, $R_7$, $R_9$ are hydrogen, and $R_8$ is hydrogen, methyl, ethyl, propyl or $C_2$-$C_3$alkyl substituted by one or two of hydroxyl, halogen or amine, then $R_1$ is not hydrogen, $C_1$-$C_2$ alkyl or $C_2$ alkyl substituted by one or two of halogen, hydroxyl or amine;
$R_3$ is H, or $C_1$-$C_6$alkyl;
$R_4$, $R_5$, $R_6$ and $R_7$ are independently hydrogen or $C_1$-$C_6$alkyl;
$R_8$ is hydrogen, $C_1$-$C_6$alkyl, $C_1$-$C_6$haloalkyl, $C_2$-$C_6$ alkenyl, $C_2$-$C_6$haloalkenyl, $C_2$-$C_6$alkynyl, $C_2$-$C_6$haloalkynyl, $C_3$-$C_6$cycloalkyl, $C_4$-$C_6$alkylcycloalkyl, aryl or aryl substituted by one to five substituents $R_{11}$, heteroaryl or heteroaryl substituted by one to five substituents $R_{11}$, heterocyclyl or heterocyclyl substituted by one to five substituents $R_{11}$;
or $R_8$ is $C_1$-$C_6$ alkyl substituted by one or more cyano, nitro, amine, N—$C_1$-$C_6$alkyl amine, N,N-di-$C_1$-$C_6$alkyl amine, hydroxyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aryl or aryl substituted by one to five substituents $R_{11}$, heteroaryl or heteroaryl substituted by one to five substituents $R_{11}$, heterocyclyl or heterocyclyl substituted by one to five substituents $R_{11}$;
each $R_{11}$ is independently cyano, nitro, amino, hydroxy, halogen, $C_1$-$C_6$alkyl, $C_1$-$C_6$haloalkyl, $C_1$-$C_4$alkoxy-$C_1$-$C_4$alkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_3$-$C_6$halocycloalkyl, $C_1$-$C_6$alkoxy, $C_1$-$C_6$haloalkoxy, $C_1$-$C_4$alkoxy-$C_1$-$C_4$-alkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, N—$C_1$-$C_6$alkylamino, N,N-di-($C_1$-$C_6$alkyl)amino, N,N-di-($C_1$-$C_6$alkyl)-aminocarbonyl, N,N-di-($C_1$-$C_6$alkyl)aminosulfonyl, $C_1$-$C_6$alkylcarbonyl, $C_1$-$C_6$alkylcarbonyloxy, $C_1$-$C_6$alkoxycarbonyl, $C_1$-$C_6$alkylcarbonylamino;
or a salt or N-oxide thereof;
excluding the following compounds wherein
X is trifluoromethyl, $R_1$ is chlorine, and $R_2$, $R_3$, $R_4$, $R_5$, $R_6$, $R_7$, $R_8$, $R_9$ are hydrogen;
X is iodine or bromine, $R_1$, $R_3$, $R_4$, $R_5$, $R_6$, $R_7$, $R_9$ are hydrogen, and $R_2$ and $R_8$ are methyl;
X is bromine, $R_1$, $R_2$, $R_4$, $R_5$, $R_6$, $R_7$, $R_9$ are hydrogen, $R_3$ is ethyl, and $R_8$ is methyl;
And X is nitro, N—$C_1$-$C_6$alkyl amine or N,N-di-$C_1$-$C_6$alkyl amine, and $R_1$, $R_2$, $R_3$, $R_4$, $R_5$, $R_6$, $R_7$, $R_8$, $R_9$ are hydrogen.

2. A compound according to claim 1, wherein
W is O;
$R_1$ is H, trifluoromethyl, cyano, halogen or methyl;
$R_2$ is H, trifluoromethyl, cyano, halogen or methyl;
X is $C_1$-$C_6$haloalkyl or cyano;
$R_3$ is H or $C_1$-$C_6$alkyl;
$R_4$, $R_5$, $R_6$ and $R_7$ are independently hydrogen or methyl;
$R_8$ is hydrogen, $C_1$-$C_6$alkyl, $C_1$-$C_6$haloalkyl, $C_2$-$C_6$ alkenyl, $C_2$-$C_6$alkynyl;
or $R_8$ is $C_1$-$C_6$ alkyl substituted by one or more $C_1$-$C_6$alkoxy, $C_1$-$C_6$alkylthio; and
$R_9$ is hydrogen.

3. A compound according to claim 2, wherein X is trifluoromethyl or cyano.

4. A compound according to claim 1, wherein $R_8$ is hydrogen, methyl, ethyl, n-propyl or iso-propyl.

5. A compound according to claim 4, wherein $R_8$ is hydrogen.

* * * * *